(12) United States Patent
Suri et al.

(10) Patent No.: US 9,828,458 B2
(45) Date of Patent: Nov. 28, 2017

(54) SILICA PARTICLES COATED WITH β-CYCLODEXTRIN FOR THE REMOVAL OF EMERGING CONTAMINANTS FROM WASTEWATER

(71) Applicant: TEMPLE UNIVERSITY—OF THE COMMONWEALTH SYSTEM OF HIGHER EDUCATION, Philadelphia, PA (US)

(72) Inventors: Rominder P. S. Suri, Audubon, PA (US); Bikash Bhattarai, Sanopokhara-makawanpur (NP)

(73) Assignee: TEMPLE UNIVERSITY—Of The Commonwealth System of Higher Education, Philadelphia, PA (US)

( * ) Notice: Subject to any disclaimer, the term of this patent is extended or adjusted under 35 U.S.C. 154(b) by 160 days.

(21) Appl. No.: 14/350,658

(22) PCT Filed: Oct. 17, 2012

(86) PCT No.: PCT/US2012/060567
§ 371 (c)(1),
(2) Date: Apr. 9, 2014

(87) PCT Pub. No.: WO2013/059285
PCT Pub. Date: Apr. 25, 2013

(65) Prior Publication Data
US 2014/0231352 A1 Aug. 21, 2014

Related U.S. Application Data

(60) Provisional application No. 61/548,031, filed on Oct. 17, 2011.

(51) Int. Cl.
*B01J 20/283* (2006.01)
*B01J 20/32* (2006.01)
(Continued)

(52) U.S. Cl.
CPC ........ *C08G 18/6484* (2013.01); *B01J 20/286* (2013.01); *B01J 20/288* (2013.01);
(Continued)

(58) Field of Classification Search
CPC ...... B01J 20/10; B01J 20/103; B01J 20/3204; B01J 20/22; B01J 20/24; B01J 20/26;
(Continued)

(56) References Cited

U.S. PATENT DOCUMENTS 4,539,399 A  9/1985  Armstrong
4,917,956 A  4/1990  Rohrbach
(Continued)

FOREIGN PATENT DOCUMENTS

JP  2003-226737 A  8/2003

OTHER PUBLICATIONS

Crini et al. Synthesis and applications of adsorbents containing cyclodextrins. J. Sep. Sci. 2002, 25, 789-813.*
(Continued)

*Primary Examiner* — Katherine Zalasky
(74) *Attorney, Agent, or Firm* — Drinker Biddle & Reath LLP

(57) ABSTRACT

Provided is a silica particle coated with β-cyclodextrin, wherein said cyclodextrin is attached to said silica particle via at least one crosslinking agent and/or at least one copolymer. Also provided are methods of removing contaminants from a flowing or stationary liquid phase comprising the step of contacting said liquid phase with the silica particle coated with β-cyclodextrin.

23 Claims, 24 Drawing Sheets

(51) Int. Cl.
| | |
|---|---|
| B01J 20/286 | (2006.01) |
| B01J 20/10 | (2006.01) |
| C02F 1/28 | (2006.01) |
| C08G 18/64 | (2006.01) |
| B01J 20/288 | (2006.01) |
| C02F 1/68 | (2006.01) |
| C07H 23/00 | (2006.01) |
| B01J 20/26 | (2006.01) |
| C02F 101/30 | (2006.01) |

(52) U.S. Cl.
CPC ....... *B01J 20/3204* (2013.01); *B01J 20/3274* (2013.01); *B01J 20/3282* (2013.01); *B01J 20/3293* (2013.01); *C02F 1/288* (2013.01); *C02F 1/683* (2013.01); *C07H 23/00* (2013.01); *B01J 20/267* (2013.01); *C02F 1/281* (2013.01); *C02F 1/285* (2013.01); *C02F 2101/305* (2013.01)

(58) Field of Classification Search
CPC ........ B01J 20/265; B01J 20/267; B01J 20/32; B01J 20/3231; B01J 20/3255; B01J 20/3246; B01J 20/3248; B01J 20/3268; B01J 20/3272; B01J 20/3274; B01J 20/3282; C09D 105/16; A61K 9/5036; A61K 9/5161; A61K 9/286; A61K 9/205; A61K 9/1652; A61K 31/724; A61K 47/40
See application file for complete search history.

(56) References Cited

U.S. PATENT DOCUMENTS

| | | | | |
|---|---|---|---|---|
| 5,098,793 | A * | 3/1992 | Rohrbach | C08B 37/0012 428/402 |
| 5,262,404 | A * | 11/1993 | Weisz | A61K 31/724 514/58 |
| 5,360,899 | A * | 11/1994 | Nussstein | B01J 20/26 536/103 |
| 6,767,507 | B1 | 7/2004 | Woo et al. | |
| 2001/0008222 | A1 | 7/2001 | Ma et al. | |
| 2008/0194784 | A1 | 8/2008 | Choi et al. | |

OTHER PUBLICATIONS

Romo et al. Application of factorial experimental design to the study of the suspension polymerization of beta-cyclodextrin and epichlorohydrin. J. Applied Polymer Science, vol. 100 (2006) 3393-3402.*
Supplementary European Search Report for EP12840955 dated Jun. 15, 2015.
Bhattarai, "Development of Novel Adsorbents for the Removal of Emerging Contaminants from Water", Thesis Submitted to the Temple University Graduate Board, (May 2011).
Oishi et al., "Removal of dissolved estrogen in sewage effluents by beta-cyclodextrin polymer". Science of the Total Environment 409(1):112-115 (2010).
Orprecio et al., "Polymer-immobilized cyclodextrin trapping of model organic pollutants in flowing water streams". J. Applied Polymer Science, 90(8):2103-2110 (2003).
Cserhati et al., "Effect of -cyclodextrin derivatives on the retention of steroidal drugs". J. Chromatography B:Biomedical sciences and applications. vol. 681, Issue 1, May 31, 1996, pp. 205-211.
Fenyvesi, "Cyclodextrin polymers in the pharmaceutical industry". J. of Inclusion Phenomena and Macrocyclic Chemistry 6(5):537-545 (1987).
Liu et al., "High performance liquid chromatography with cyclodextrin and calixarene macrocycle bonded silica stationary phases for separation of steroids". Talanta 66(2): 479-486 (2005).

Pluemsab et al., "Cyclodextrin-linked alginate beads as supporting materials for Sphingomonas cloacae, a nonylphenol degrading bacteria". Biores Tech 98(11):2076-2081 (2007).
Salipira et al., "Cyclodextrin polyurethanes polymerized with carbon nanotubes for the removal of organic pollutants in water". Water SA 34(1)113-118 (2008).
Mamba et al., "Monofunctionalized cyclodextrin polymers for the removal of organic pollutants from water". Environ Chem Lett 5:79-84 (2007).
Arkas et al., "Organic/Inorganic hybrid filters based on dendritic and cyclodextrin "nanosponges" for the removal of organic pollutants from water". Environ. Sci. Technol. 40:2771-2777 (2006).
Jiang et al., "New amphoteric flocculant containing β-cyclodextrin, synthesis, characterization and decolorization properties". J. Hazardous Materials 173:298-304 (2010).
Badruddoza et al., "Synthesis of carboxymethyl-beta-cyclodextrin conjugated magnetic nano-adsorbent for removal of methylene blue". Colloids and Surfaces A: Physicochem. Eng. Aspects 367:85-95 (2010).
Ozmen et al., "A Calix[4]arene oligomer and two p-cyclodextrin polymers: synthesis and sorption studies of azo dyes". J. Macromolecular Science, Part A: Pure and Applied Chemistry 44:167-173 (2007).
Mamba et al., "Cyclodextrin nanosponges in the removal of organic matter to produce water for power generation". Water SA 34(5):657-660 (2008).
Nyugen, "Surface functionalization of nano-magnetic particle with beta cyclodextrin and its use in bio-molecule refolding process". National University of Singapore thesis. (2007).
Bambo, "Synthesis, characterization and application of nanoporous cyclodextrin polymers". University of Johannesburg. (2007).
Savage et al., "Nanomaterials and water purification: opportunities and challenges". J. Nano. Res. 7: 331-342 (2005).
Caliman et al., "Pharmaceuticals, Personal Care Products and Endocrine Disrupting Agents in the Environment". Clean 37(4-5), 277-303 (2009).
Yamasaki et al., "Efficient phenol removal of wastewater from phenolic resin plants using crosslinked cyclodextrin particles". J Chem Technol Biotechnol 81:1271-1276 (2006).
Yamasaki et al., "Preparation of crosslinked β-cyclodextrin polymer beads and their application as a sorbent for removal of phenol from wastewater". J Chem Technol Biotechnol 83:991-997 (2008).
Zhao et al., "Water-insoluble b-cyclodextrin polymer crosslinked by citric acid: synthesis and adsorption properties toward phenol and methylene blue", J Incl Phenom Macrocyl Chem 63: 195-201 (2009).
Yang et al., "Inclusion complexes of bisphenol a with cyclomaltoheptaose (β-cyclodextrin): solubilization and structure", Carbohydrate Research 343(14):2439-2442 (2008).
Wang et al., "A Reversible Fluorescence Sensor based on insoluble β-cyclodextrin polymer for direct determination of bisphenol A (BPA)", Sensors and Actuators B 114:565-572 (2006).
Crini, "Recent development in polysaccharide-based materials used as absorbents in wastewater treatment", Prog. Polym. Sci. 30 38-70 (2005).
Khan et al., "Methods for selective modification of cyclodextrins", Chem. Rev. 98, 1977-1996 (1998).
Sugiura et al., "Immobilized β-cyclodextrin—Preparation with varous crosslinking reagents and the guest binding-properties", Bulletin of the Chemical Socitey of Japan 62(5):1643-1651 (1989).
Crini, "Studies on adsorption of dyes on beta-cyclodextrin polymer", Bioresource Technology 90(2):193-198 (2003).
Girek et al., "Polymerisation of b-cyclodextrin with succinic anhydride. Synthesis, characterisation, and ion flotation of transition metals", Carbohydrate Polymers 59(2):211-215 (2005).
Carbonnier et al., "Coating of Porous Silica Beads by in Situ Polymerization/Crosslinking of 2-Hydroxypropyl β-Cyclodextrin for Reversed-Phase High Performance Liquid Chromatography Applications", J. of Appl. Polym. Sci. 90:1419-1426 (2004).
Crini et al., "Separation of Structural Isomers Using Cyclodextrin-Polymers Coated on Silica Beads", Chromatographia 40(5-6):296-302 (1995).

(56) References Cited

OTHER PUBLICATIONS

Phan et al., "New silica gels functionalized with 2-hydroxy-3-methacryloyloxypropyl-b-cyclodextrin using coating or grafting methods", Physical Chemistry Chemical Physics 1(22):5189-5195 (1999).

Crini et al., "Beta-cyclodextrin-copolymers coated on silica beads: Synthesis, characterization and retention behavior in HPLC", Chromatographia 50 (11-12):661-669 (1999).

Phan et al., "Synthesis and Characterization of Silica Gels Functionalized with Monochlorotriazinyl β-Cyclodextrin and their Sorption Capacities towards Organic Compounds", Journal of Inclusion Phenomena and Macrocyclic Chemistry 38 (1-4): 345-359 (2000).

Phan et al., "The removal of organic pollutants form water using new-silica supported β-cyclodextrin derivatives", Reactive & Functional Polymers 52:117-125 (2002).

Carbonnier et al., "Preparation, characterisation and enantioselective separation properties of a chiral stationary phase based on silica beads coated with a 2-hydroxypropyl-β-cyclodextrin polymer", E-Polymers, article No. 004 (2003).

Ponchel et al., "Cyclodextrin silica-based materials: advanced characterizations and study of their complexing behavior by diffuse reflectance UV—Vis spectroscopy", Microporous and Mesoporous Materials 75(3):261-272 (2004).

Saikia et al., "Studies on adsorption of amino acids on β-cyclodextrin bonded to silica particles", Colloids and Surfaces A:Physicochemical and Engineering Aspects 329(3):177-183 (2008).

Fujimoto et al. "An Attempt Directed toward Enhanced Shape Selectivity in Reversed-Phase Liquid Chromatography: Preparation of the Dodecylaminated Beta-Cyclodextrin-Bonded Phase", Analytical Sciences, (Jan. 2002), vol. 18: 65-68.

Bertolla, "Monofunctionalizations of beta-cyclodextrin, conjugation with recognition pattersn, biological evaluation", Univeristy of Namur Doctoral Thesis, (2010).

* cited by examiner

US 9,828,458 B2

SILICA PARTICLES COATED WITH β-CYCLODEXTRIN FOR THE REMOVAL OF EMERGING CONTAMINANTS FROM WASTEWATER

CROSS-REFERENCE TO RELATED APPLICATIONS

This application claims the benefit of U.S. Provisional Application No. 61/548,031, filed Oct. 17, 2011, the entire disclosure of which is incorporated herein by reference.

STATEMENT REGARDING FEDERALLY FUNDED RESEARCH

This invention was made with government support under Grant No. IP-0855881 awarded by the National Science Foundation (NSF). The government has certain rights in the invention.

FIELD

The present invention relates to silica particles coated with β-cyclodextrin and methods of using the same to remove contaminants from liquids such as wastewater.

BACKGROUND

Nanoparticles Comprising Silica Particles Coated with β-Cyclodextrin

Nanoparticles have shown great potential as water-purification catalysts and redox active media for the treatment of organic and inorganic pollutants (Savage et al., Nanomaterials and water purification: opportunities and challenges. *J. Nano. Res.* 7: 331-342 (2005)). The property of cyclodextrins to form inclusion complexes with various molecules through host-guest interactions (Caliman et al. *Clean* 37(4-5), 277-303 (2009)) has made them useful compounds for the removal of a number of contaminants from water and wastewater (Yamasaki et al. *J Chem Technol Biotechnol* 81:1271-1276 (2006), Mhlanga et al. *J Chem Technol Biotechnol* 82:382-388 (2007), Yamasaki et al. *J Chem Technol Biotechnol* 83:991-997 (2008), Zhao et al. *J Incl Phenom Macrocyl Chem* (2009) 63: 195-201). The formation of inclusion complexes with bisphenol A (BPA) has been reported in solution phase (Liu et al. *Carbohydrate Research* 343(14):2439-2442 (2008)) and in solid phase by using β-cyclodextrin-polymer (β-CD-polymer) (Wang et al. *Sensors and Actuators B* 114:565-572 (2006)). The commonly available different types of cyclodextrins are α-cyclodextrin, β-cyclodextrin (β-CD) and γ-cyclodextrin which consist of six, seven and eight α-1,4 linked D(C)-glucopyranose units, respectively (Crini, G. *Prog. Polym. Sci.* 30 38-70 (2005)). The presence of hydroxyl groups at position 2, 3, and 6 in the glucose unit can be used for the structural modifications of cyclodextrins (Khan et al. *Chem. Rev.* 98, 1977-1996 (1998)) in order to obtain insoluble derivatives of cyclodextrins (Sugiura et al. *Bulletin of the Chemical Socitey of Japan* 62(5):1643-1651 (1989), Crini, G. *Bioresource Technology* 90(2):193-198 (2003), Girek et al. *Carbohydrate Polymers* 59(2):211-215 (2005), Yamasaki et al. *J Chem Technol Biotechnol* 83:991-997 (2008)) and to immobilize them onto inorganic supports like silica (Armstrong, D. W. U.S. Pat. No. 4,539,399 (1985), Crini et al. *Chromatographia* 40(5-6):296-302 (1995), Phan et al. *Physical Chemistry Chemical Physics* 1(22):5189-5195 (1999), Crini et al. *Chromatographia* 50 (11-12):661-669 (1999), Morcellet et al. *Journal of Inclusion Phenomena and Macrocyclic Chemistry* 38 (1-4): 345-359 (2000), Phan et al. *Reactive & Functional Polymers* 52:117-125 (2002), Carbonnier et al. *E-Polymers*, article no. 004 (2003), Ponchel et al. *Microporous and Mesoporous Materials* 75(3):261-272 (2004), Saikia et al. *Colloids and Surfaces A: Physicochemical and Engineering Aspects* 329(3):177-183 (2008)). The chemically bonded organic-inorganic particles combine the advantageous properties of both inorganic support (excellent mechanical strength) and bonded organic compounds (high efficiency, reproducibility and selectivity) (Carbonnier et al. *J. of Appl. Polym. Sci.* 90:1419-1426 (2004)).

SUMMARY

Provided is a silica particle coated with β-cyclodextrin polymer, wherein the β-cyclodextrin polymer is formed by polymerizing β-cyclodextrin with (i) hexamethylene diisocyanate (HMDI), wherein the molar ratio of β-cyclodextrin:HMDI in the polymerization is from about 1:7 to about 1:15 and wherein the molar ratio of β-cyclodextrin:silica in the polymerization is from about 1:15 to about 1:30; or (ii) epichlorohydrin (EPI), wherein the molar ratio of β-cyclodextrin:EPI in the polymerization is from about 1:7 to about 1:9 and wherein the molar ratio of β-cyclodextrin:silica in the polymerization is from about 1:83 to about 1:125. In some preferred embodiments of option (i) the molar ratio of β-cyclodextrin:silica in the polymerization is about 1:19.

Provided is a silica particle modified with a functional group on its surface and coated with β-cyclodextrin, wherein the β-cyclodextrin is attached to the silica particle via a chemical bond to the functional group on the surface of the silica. In some embodiments, the functional group is formed by chemical reaction of the silica with a compound selected from the group consisting of glycidoxypropyl trimethoxysilane (GPTS) and aminopropyl triethoxysilane (APTES).

Provided is a silica particle modified with a functional group on its surface and coated with β-cyclodextrin polymer, wherein the β-cyclodextrin polymer is formed by polymerizing β-cyclodextrin with HMDI or EPI and wherein the β-cyclodextrin polymer is attached to the silica particle via a chemical bond to the functional group on the surface of the silica. In some embodiments the functional group is formed by chemical reaction of the silica with a compound selected from the group consisting of GPTS and APTES.

Provided is a process for producing a silica particle coated with β-cyclodextrin comprising coating silica particles with β-cyclodextrin; and polymerizing the β-cyclodextrin with HMDI to form HMDI-crosslinked β-cyclodextrin polymer; wherein the molar ratio of 3-cyclodextrin:HMDI in the polymerization is from about 1:7 to about 1:15 and wherein the molar ratio of β-cyclodextrin:silica in the polymerization is from about 1:15 to about 1:30. In some preferred embodiments the molar ratio of β-cyclodextrin:silica in the polymerization is about 1:19.

Provided is a process for producing a silica particle coated with β-cyclodextrin comprising coating silica particles with β-cyclodextrin; and polymerizing the β-cyclodextrin with EPI to form EPI-crosslinked 3-cyclodextrin polymer; wherein the molar ratio of β-cyclodextrin:EPI in the polymerization is from about 1:7 to about 1:9 and wherein the molar ratio of β-cyclodextrin:silica in the polymerization is from about 1:83 to about 1:125.

Provided is a process for producing a silica particle modified with a functional group on its surface and coated with β-cyclodextrin, wherein the β-cyclodextrin is attached to the silica particle via a chemical bond to the functional group on the surface of the silica, comprising reacting a silica particle with a compound selected from the group consisting of GPTS and APTES to form a functionalized silica particle; and reacting β-cyclodextrin with the functionalized silica particle to form a functionalized silica particle coated with β-cyclodextrin.

Provided is a process for producing a silica particle modified with a functional group on its surface and coated with β-cyclodextrin, wherein the β-cyclodextrin is attached to the silica particle via a chemical bond to the functional group on the surface of the silica, comprising reacting β-cyclodextrin with a compound selected from the group consisting of GPTS and APTES to form a functionalized β-cyclodextrin; and reacting a silica particle with the functionalized β-cyclodextrin to form a functionalized silica particle coated with β-cyclodextrin.

Provided is a process for producing a silica particle modified with a functional group on its surface and coated with β-cyclodextrin, wherein the β-cyclodextrin is polymerized via HMDI or EPI and wherein the polymerized β-cyclodextrin is attached to the silica particle via a chemical bond to the functional group on the surface of the silica, comprising reacting β-cyclodextrin and HMDI or EPI to form a β-cyclodextrin polymer; separately reacting the silica particle with a compound selected from the group consisting of GPTS and APTES to make a functionalized silica particle; and coating the functionalized silica particle with the β-cyclodextrin polymer.

Provided is a method of removing contaminants from a liquid comprising the step of contacting the liquid with the silica particle coated with β-cyclodextrin of any one of the previous embodiments. In preferred embodiments, the liquid is flowing. In yet further preferred embodiments, the flowing liquid is mixed with the silica particle coated with β-cyclodextrin and the mixture is agitated. In some preferred embodiments, the silica particle coated with β-cyclodextrin is contained in a column. In further preferred embodiments, the liquid is stationary. In yet further preferred embodiments, the stationary liquid is mixed with the silica particle coated with β-cyclodextrin and the mixture is agitated.

In some embodiments, the contaminant is a steroid hormone. In preferred embodiments, the steroid hormone is an estrogen, a progestrogen or a testosterone. In further preferred embodiments, the steroid hormone is selected from the group consisting of 17β-estradiol, 17α-ethynylestradiol, estriol, 17α-estradiol, trimegestrone, estrone, 17α-dihydroequilin, medrogestone, progesterone, gestodone, norgestrel, equilin, testosterone, desogestrel and etonorgestrel.

In some embodiments, the contaminant is a phenol. In preferred embodiments, the phenol is bisphenol A (BPA).

In some embodiments, the contaminant is a perfluorocompound. In preferred embodiments, the perfluorocompound is selected from the group consisting of tridecafluorononanoic acid, perfluoroheptanoic acid, undecafluorohexanoic acid, perfluorodecanoic acid, heptafluorooctane salt and perfluorooctanoic acid (PFOA).

As envisioned in the present invention with respect to the disclosed compositions of matter and methods, in one aspect the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

DEFINITIONS

Figure 1A:
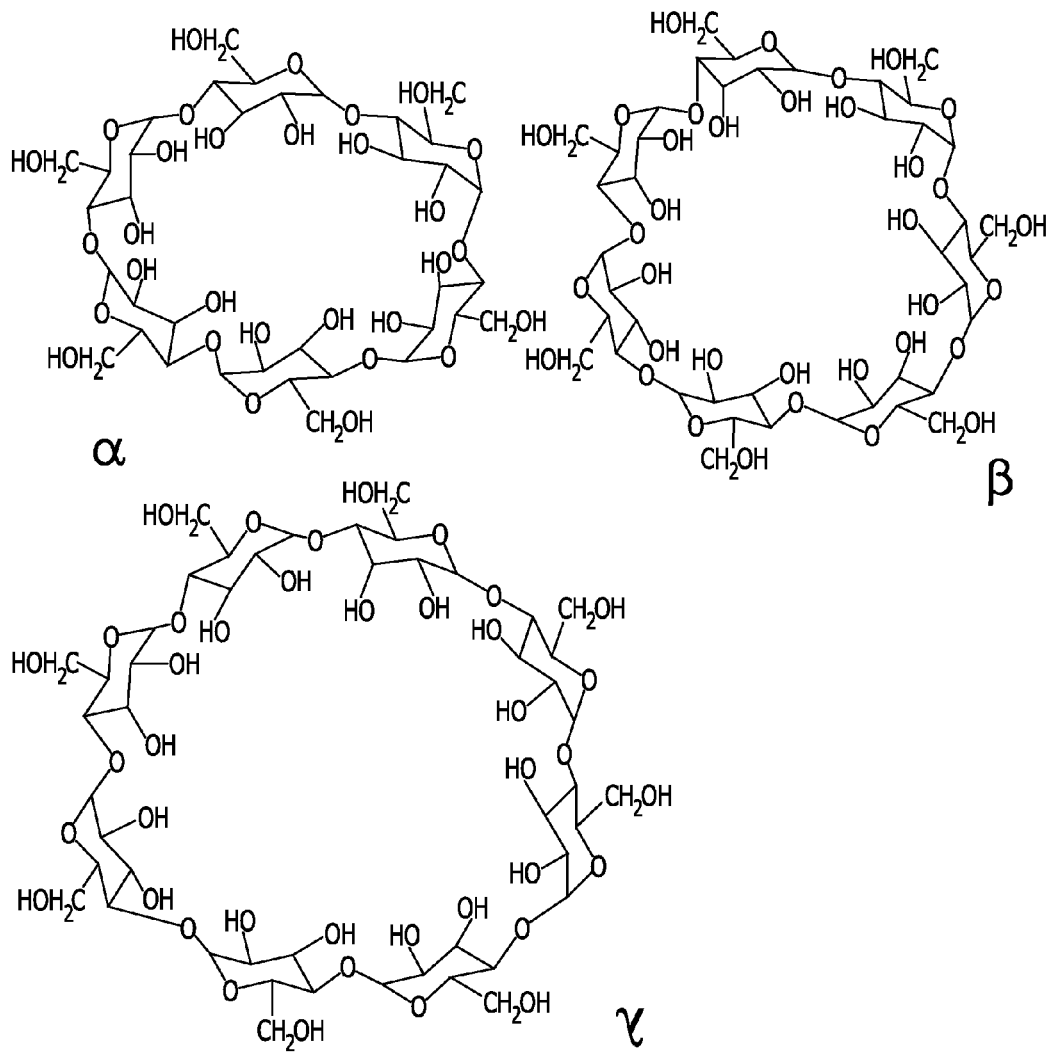
FIG. 1A illustrates the three smallest cyclodextrins, α-cyclodextrin, β-cyclodextrin and γ-cyclodextrin.
Figure 1B:
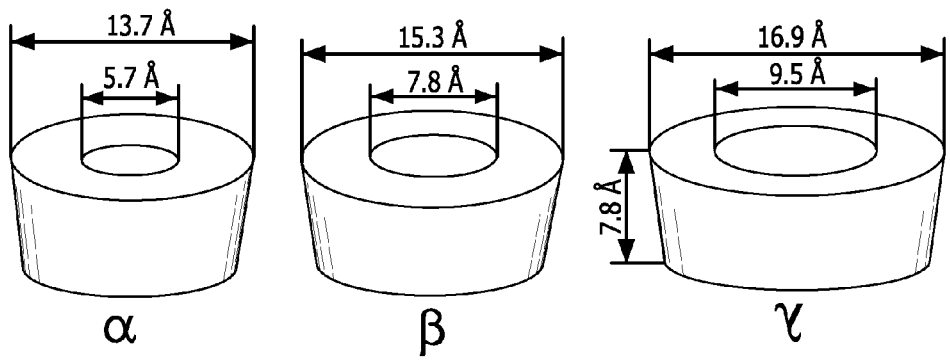
FIG. 1B illustrates their dimensions. The depth of the cavity is about 7.8 Ångstroms for the three cyclodextrins and the width of the cavity ranges from about 5 to about 9 Ångstroms.

The articles "a" and "an" are used herein to refer to one or to more than one (i.e. to at least one) of the grammatical object of the article. By way of example, "an element" means one element or more than one elements.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

The phrase "β-cyclodextrin (β-CD)" refers to a ring structure of seven glucopyranoside units. It can be topologically represented as a toroid with the larger and the smaller openings of the toroid exposing to the solvent secondary and primary hydroxyl groups. The interior of the β-cyclodextrin ring is less hydrophilic than the aqueous environment and can therefore make complexes with other hydrophobic molecules. However, the exterior of the β-cyclodextrin ring is sufficiently hydrophilic to make cyclodextrin or its complexes water soluble.

The phrase "crosslinking agent" refers to a molecule that links one polymer subunit to another, to form a polymer. Crosslinking agents can form covalent bonds or ionic bonds to the polymer chain. Crosslinks can be formed by chemical reactions that are initiated by heat, pressure, change in pH or radiation, for example. Examples of crosslinking agents include, but are not limited to, hexamethylene diisocyanate (HMDI) and epichlorohydrin (EPI).

The phrase "copolymer" refers to a molecule that links β-cyclodextrin to the silica particle. In some embodiments, the copolymer is a silane. In preferred embodiments, the copolymer is glycidoxypropyl trimethoxysilane (GPTS) or aminopropyl triethoxysilane (APTS).

The phrase "steroid hormone" refers to a steroid that acts as a hormone. Steroid hormones can be grouped into five groups by the receptors to which they bind: glucocorticoids, mineralocorticoids, androgens, estrogens and progestrogens. Steroid hormones help control metabolism, inflammation, immune functions, salt and water balance, development of sexual characteristics, and the ability to withstand illness and injury. Steroid hormones can be naturally made by the body or may be artificially produced. Examples of steroid hormones include, but are not limited to, 17β-estradiol, 17α-ethynylestradiol, estriol, 17α-estradiol, trimegestrone, estrone, 17α-dihydroequilin, medrogestone, progesterone, gestodone, norgestrel and equilin.

The phrase "estrogens" refers to a group of compounds named for its importance in the estrous cycle of humans or other animals. They are the primary female sex hormones. Natural estrogens are steroid hormones, while some synthetic ones are non-steroidal. Examples of estrogens include, but are not limited to 17β-estradiol, 17α-ethynylestradiol, estriol, and 17α-estradiol.

The phrase "progesterones," "progestrogens" or "progestogens" refers to a group of hormones that are named for their function in maintaining pregnancy (pro-gestational), although they are also present at other phases of the estrous and menstrual cycles. The progestrogen class of hormones includes all steroids with a pregnane skeleton, that is, both naturally occurring and synthetic ones. Exogenous or synthetic hormones are usually referred to as progestins. An example of a progestrogen is progesterone.

LIST OF ACRONYMS

APTES Aminopropyl triethoxysilane
DMF Dimethylformamide
DMS Dimethyl sulfoxide
EPI Epichlorohydrin
GPTS Glycidoxypropyl trimethoxysilane
HMDI Hexamethylene diisocyanate
MQ Milli-Q water
Silica Mesh size silica (40×100)
   US sieve size 10-200
β-CD β-Cyclodextrin

DETAILED DESCRIPTION

Provided is a silica particle coated with β-cyclodextrin and method for removing contaminants from a liquid using the coated particle.

Synthesis of Silica Particles Coated with β-Cyclodextrin.

In order to coat β-cyclodextrin onto silica, four different approaches were used:

1. The silica particle was coated with β-cyclodextrin that was polymerized with a cross-linking agent such as HMDI or EPI. The solid hard product thus obtained was crushed and sieved to obtain coated silica particles of the desired size.

2. The silica particle was modified with a functional group and was then reacted with β-cyclodextrin, wherein the β-cyclodextrin was attached to the silica particle via a chemical bond to the functional group on the surface of the silica particle. The silica particle was functionalized or silanized by reaction with a compound such as GPTS or APTES.

3. The β-cyclodextrin was modified with a functional group and was then reacted with a silica particle, wherein the silica particle was attached to the β-cyclodextrin via a chemical bond to the functional group on the surface of the β-cyclodextrin. The β-cyclodextrin was functionalized or silanized by reaction with a compound such as GPTS or APTES.

4. The silica particle was modified with a functional group on its surface and was then coated with β-cyclodextrin, wherein the β-cyclodextrin was polymerized via a cross-linking agent such as HMDI or EPI and wherein the polymerized β-cyclodextrin was attached to the silica particle via a chemical bond to the functional group on the surface of the silica. The silica particle was functionalized or silanized by reaction with a compound such as GPTS or APTES.

Cross-linking agents that may be used to make silica particles coated with β-cyclodextrin comprise HMDI, EPI, Toluene diisocyanate (TDI), Citric acid, Polyethylenimine (PEI), Poyvinyl alcohol (PVA) and Butyl methacrylate.

Compounds that may be used to functionalize or silanize silica particles comprise GPTS, APTES, Tetraethyl orthosilicate (TEOS) and Methacryloxypropylsilane.

The size of the silica particles can range from about US Sieve size 10 to about 200. The size of the coated silica particles can range from about US Sieve size 10 to about 200.

Methods for Removing Contaminants from a Liquid Using the Silica Particles Coated with β-Cyclodextrin.

The silica particles coated with β-cyclodextrin may be used to remove contaminants from liquid that is flowing. The coated silica particles may be contained in a column, such as a chromatography column. The liquid may flow through the column, and the contaminants may be absorbed by the coated silica particles in the column. The flow-through liquid may then be collected or it may be routed to be passed through the same column or through a different column for further removal of contaminants. Another method for removing contaminants from flowing liquid using the β-cyclodextrin-coated silica particles is by allowing the liquid to flow into containers containing the coated particles, mixing the liquid with the coated particles, and agitating the mixture. The liquid may then be collected or it may be routed to flow into further containers containing coated particles for further removal of contaminants.

The silica particles coated with β-cyclodextrin may be used to remove contaminants from liquid that is stationary. The liquid may be mixed with the β-cyclodextrin-coated silica particles and the mixture may be agitated. The liquid may then be collected or it may be mixed with further coated particles for further removal of contaminants.

The duration of the process may vary. Preferably, the removal of contaminants from the liquid will proceed until the level of contaminant present in the liquid has been reduced to the desired level. The temperature and other conditions may be varied and optimized to obtain maximum removal of contaminant from the liquid.

The process may be carried out in a continuous or semi-continuous fashion. Alternatively, the process may be carried out in batch operation. As the contaminant is being removed from the liquid, the level of contaminant in the liquid may be monitored by methods known to a person skilled in the art. For example, the level of contaminant in the liquid may be measured by liquid chromatography, gas chromatography, mass spectroscopy, UV spectrometry or combinations thereof carried out on a sample of the liquid obtained during the removal process.

The liquid from which contaminants are removed by the present methods can be aqueous or non-aqueous. The liquid may be from a natural source or from a non-natural source. The liquid may be wastewater. The wastewater may be from a natural source such as a stream, river, aquifer, pond, or lake. The wastewater may be from a non-natural source such as municipal wastewater, a septic tank or industrial waste.

The silica particles coated with β-cyclodextrin may be regenerated after use to remove contaminants. The regeneration may be carried out with an organic solvent such as methanol or inorganic liquids such as hydrochloric acid or sodium hydroxide.

EXAMPLES

Example 1: Equilibrium Studies with 17β-Estradiol

A. Synthesis of Insoluble Form of β-CD:
Materials

β-Cyclodextrin (β-CD) (99%), and dimethyl sulfoxide (DMSO) were purchased from Fisher Scientific. The cross-linking agents (epichlorohydrin (EPI), hexamethylene diisocyanate (HMDI)) and the copolymers (glycidoxypropyl trimethoxysilane (GPTS), aminopropyl triethoxysilane (APTES)) were obtained from Sigma-Aldrich. Silica (40-100 mesh size) and the solvents for β-CD (dimethyl formamide (DMF) and NaOH) were also purchased from Sigma-Aldrich.

Methods

Adsorbent A1:

2.27 gm of β-CD was dissolved in 11 ml of DMSO. To this, 3 gm of silica was added and stirred at 60° C. for 15 min. 2.3 ml HMDI was added dropwise and the mixture was left stirring 60° C. for 2 hrs. The mixture was then transferred to the oven at 60° C. for 18 hrs. A solid hard product was obtained which was crushed and sieved using mesh size 18×35. Thus obtained adsorbent was washed with MilliQ (MQ) water and methanol and dried at 60° C. overnight under vacuum.

Adsorbent A2:

2.27 gm of β-CD was dissolved in 6 ml of NaOH (30% w/w). 15 gm of silica was added and the mixture was stirred at 60° C. for 15 min. 1.2 ml EPI was added dropwise and the mixture was left stirring 60° C. for 3 hrs. The mixture was then transferred to an oven at 90° C. for 18 hrs. The final solid polymer was crushed and sieved using mesh size 18×35. Thus obtained adsorbent was washed with MQ water and methanol and dried at 60° C. overnight under vacuum.

Adsorbent A3:

2.27 gm of β-CD was dissolved in 12 ml of dimethyl formamide (DMF) in the presence of sodium metal (0.1 g). 10 gm of silica was added to the mixture and it was stirred at 60° C. for 15 min. 1.2 ml EPI was added dropwise and the mixture was left stirring at 60° C. for 6 hrs. The mixture was then transferred to an oven at 90° C. for 16 hrs. A solid hard product was obtained which was crushed and sieved using mesh size 18×35. The adsorbent thus obtained was washed with MQ water and methanol and dried at 60° C. overnight under vacuum.

Preparation of Adsorbents B1-B5 and C1-C4 with Silanized Silica.

Preparation of Silanized Silica:

80 g of silica (preheated at 140° C. for 16 hrs) was reacted with 150 ml of GPTS and APTES separately to obtain two different types of silanized silica. The reaction was left at 70°

C. under continuous stirring. The obtained product was washed with toluene, acetone, and methanol and left in the oven at 120° C. for 18 hrs.

Adsorbent B1-B4:

10 g of silanized silica (with GPTS) was mixed in 50 ml deionized (DI) water to which 1 g of $K_2S_2O_8$ was added as an initiator. The mixture was allowed to react with 3 g of β-CD (after dissolving in 13 ml DMF) by adding dropwise. The mixture was stirred at 60° C. for 16 hrs and then washed with DI water. The adsorbent thus obtained was dried overnight at 60° C. (Adsorbent B1). The same procedure was followed with another silanized silica (with APTES) (Adsorbent B2). Adsorbents B3 (with GPTS) and B4 (with APTES) were prepared using the same procedure but in this method, 8 ml of NaOH (30% w/w) was used instead of DMF to dissolve β-CD.

Adsorbent B5:

2.27 gm of n-CD was dissolved in 12 ml of DMF in presence of sodium metal (0.1 g). 3.3 ml of GPTS was added to the solution and was allowed to react for 3 hrs at 70° C. To this solution, 10 gm of silica was added and stirred at 70° C. for 3 hrs. The mixture was transferred to oven at 80° C. for 16 hrs. The obtained adsorbent was washed with DMF, methanol and acetone and finally dried in the oven at 120° C. for 15 hrs.

Adsorbents C1 and C2:

2.27 gm of β-CD was dissolved in 6 ml of NaOH (30% w/w). To this, 1.2 ml EPI was added dropwise and the mixture was left stirring 60° C. for 30 min. To this mixture, 10 g of silanized silica (with GPTS) was added under continuous stirring at 60° C. for 5 hrs. The obtained adsorbent (adsorbent C1) was oven dried at 120° C. for 15 hrs. Same procedure was followed by using APTES silanized silica for adsorbent C2.

Adsorbents C3 and C4:

2.27 gm of β-CD was dissolved in 12 ml of DMF in presence of sodium metal (0.1 g). 2.3 ml HMDI was added dropwise and the mixture was left stirring 60° C. for 30 mins. To this mixture, 10 gm of silanized silica (with GPTS) was added under continuous stirring at 60° C. for 5 hrs. The adsorbent thus obtained (adsorbent C3) was oven dried at 120° C. for 15 hrs. The same procedure was followed by using APTES silanized silica for adsorbent C4.

Analysis of Estrogens:

Equilibrium studies with different compounds of interest were carried out in batch conditions. 500 ml amber bottles were used to carry out the equilibrium studies. The bottles were filled with estrogen contaminants of desired concentrations and the dosages were varied. The samples were allowed to shake for 24 or 48 hours at 140 to 170 rpm at room temperature. The removal efficiencies of the adsorbents for the given contaminants were calculated based on the final concentrations of the samples with respect to the control sample (blank).

Solid phase extraction (SPE) was used for extracting estrogens from the solution for gas chromatograph-mass spectrometer (GC-MS) analysis. In brief, the sample was passed through an SPE Varian Bond Elute C-18 adsorbent cartridge, eluted with methanol and the eluent was completely dried in an evaporator (Genevac EZ-2), and then derivatized by using bis (trimethylsilyl) trifluoro-acetamide. Analysis was performed on a GC/MS, using a Pursuit DB-225 MS capillary column (30 m×0.25 mm×0.25 µm) in a splitless mode as described elsewhere. Chimchirian et al. *Water Environment Research* 79(9):969-974 (2007). Helium was used as the carrier gas.

Results for 17β-Estradiol 0.2 gm of the adsorbents were suspended in 200 ml of 17β-estradiol (25 ppb) and placed on a shaker at 140 rpm for 24 hours at room temperature. The concentrations of 17β-estradiol were analyzed using UPLC/MS/MS. For the analysis, a calibration curve was prepared with estrone-3-methyl ether as an internal standard.

TABLE 1

Removal efficiencies of different adsorbents

| Sample No. | Adsorbent | Initial conc. (ppb) | Dosage (g/L) | Initial pH | Final pH | Removal % |
|---|---|---|---|---|---|---|
| 1 | A1 | 25 | 1 | 6.4 | 6.8 | 94 |
| 2 | A2 | 25 | 1 | 6.3 | 6.0 | 72 |
| 3 | A3 | 25 | 1 | 6.3 | 5.8 | 59 |
| 4 | B1 | 25 | 1 | 6.4 | 6.8 | 46 |
| 5 | B2 | 25 | 1 | 6.4 | 6.8 | 43 |
| 6 | B3 | 25 | 1 | 6.4 | 6.7 | 12 |
| 7 | B4 | 25 | 1 | 6.4 | 6.1 | 11 |
| 8 | B5 | 25 | 1 | 6.3 | 6.1 | 28 |
| 9 | C1 | 25 | 1 | 6.5 | 6.0 | 47 |
| 10 | C2 | 25 | 1 | 6.3 | 6.2 | 48 |
| 11 | C3 | 25 | 1 | 6.3 | 6.2 | 69 |
| 12 | C4 | 25 | 1 | 6.3 | 6.8 | 58 |

From the table above, it can be seen that adsorbents A1 and A2 have the maximum removal capacity under the given conditions which are 94% and 72% respectively. Therefore, these products were chosen to carry out the equilibrium studies with the target compounds.

Equilibrium Studies with 17β Estradiol

The adsorption equilibrium studies with adsorbent A1 were carried out for the removal of 17β-estradiol with an initial concentration of 100 ppb and sample volume of 400 ml. At the same time, the removal efficiency of the adsorbent was also compared with that of Silica (40-100 mesh size) at a given dosage.

TABLE 2

Equilibrium studies with adsorbent A1

| Adsorbent | Sample No. | Dosage (g/L) | Removal % |
|---|---|---|---|
| A1 | 1 | 0.2 | 76.1 |
|  | 2 | 0.4 | 91.2 |
|  | 3 | 0.6 | 93.9 |
|  | 4 | 0.8 | 94.6 |
|  | 5 | 1.0 | 97.0 |
|  | 6 | 1.5 | 97.2 |
|  | 7 | 2.0 | 97.3 |
| Silica | 8 | 1.5 | 8.0 |

The equilibrium studies showed that at a dosage of 1.5 g/L, maximum removal of 97% was observed (Table 2). On the other hand, no significant removal was observed with the silica as an adsorbent. This result confirms that the removal of the estrogen from the water is due to the presence of β-cyclodextrin with very minimum or no contribution from the silica present in the product.

Figure 2A:
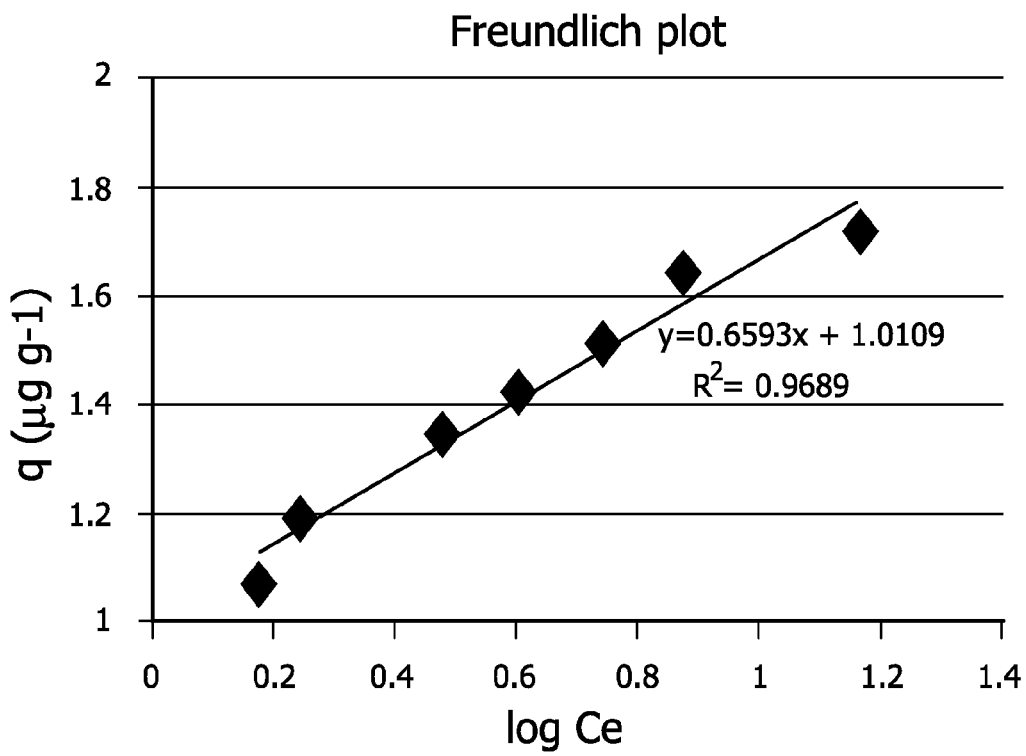
FIG. 2A illustrates a Freundlich isotherm model with adsorbent A1 (prepared with hexamethylene diisocyanate (HMDI) crosslinker; see Example 1) (k=10.3 and n=1.4, wherein k, n are constants whose values depend upon adsorbent and adsorbate at a particular temperature) (initial concentration of 17 β-estradiol 100 ppb).
Figure 2B:
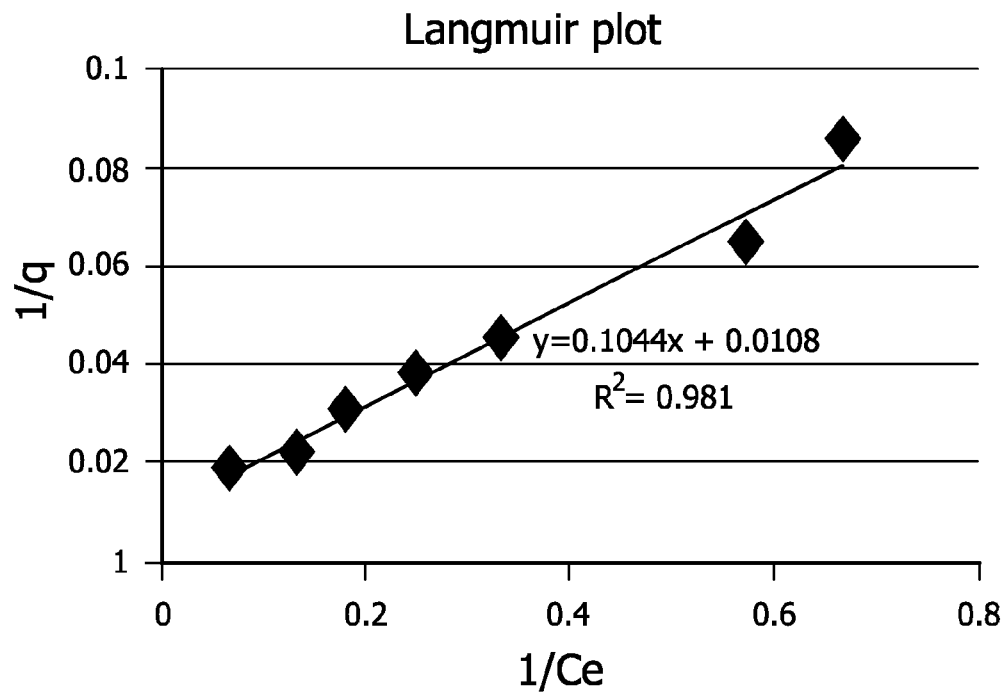
FIG. 2B: illustrates a Langmuir isotherm model with adsorbent A1 (Qm=92.6 and b=0.1, wherein Qm is a constant relating to capacity of adsorption of the adsorbent and b is an equilibrium constant) (initial concentration of 17β-estradiol 100 ppb).

The results showed a good fit to both Langmuir and Freundlich isotherm models as shown in FIG. 2.

Adsorption equilibrium studies with adsorbent A2 for the removal of 17β-estradiol (initial conc: 100 ppb & sample volume: 400 ml) showed the maximum removal of 78% at a dosage of 2 g/L (Table 3). There was no significant removal of estrogen in the presence of silica only.

TABLE 3

Equilibrium studies with adsorbent A2

| Adsorbent | Sample No. | Dosage (g/L) | Removal (%) |
|---|---|---|---|
| A2 | 1 | 0.4 | 58 |
|  | 2 | 0.6 | 53 |
|  | 3 | 0.8 | 69 |
|  | 4 | 1 | 67 |
|  | 5 | 1.5 | 74 |
|  | 6 | 2 | 78 |
| Silica | 7 | 1 | 3 |

Figure 3A:
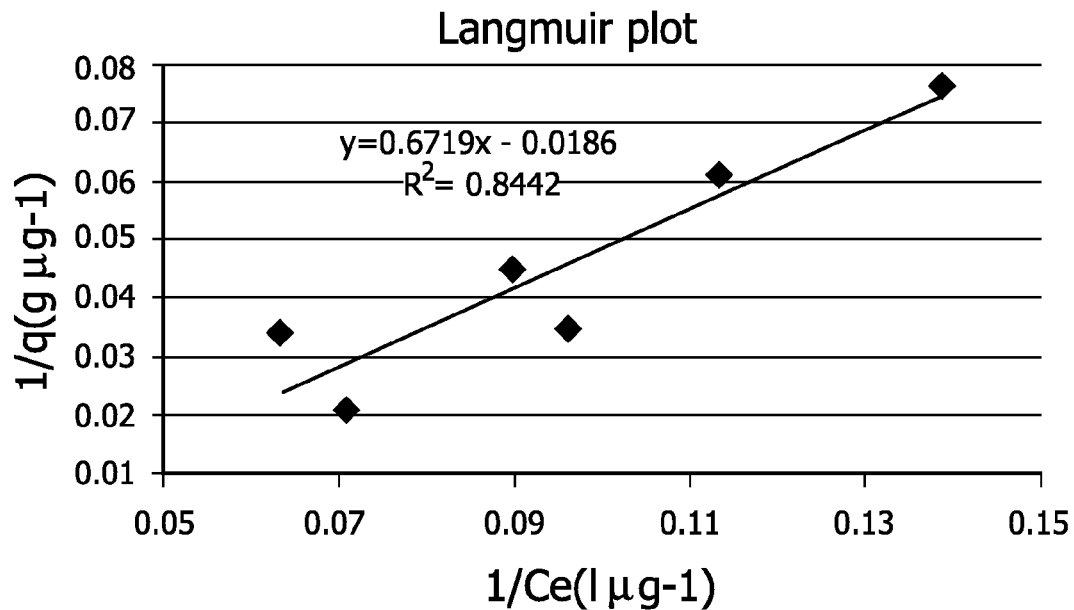
FIG. 3A illustrates a Langmuir isotherm model with adsorbent A2 (prepared with epichlorohydrin (EPI) crosslinker, see Example 1) (Qm=−53.8 and b=−0/03) (initial concentration of 17β-estradiol 100 ppb).
Figure 3B:
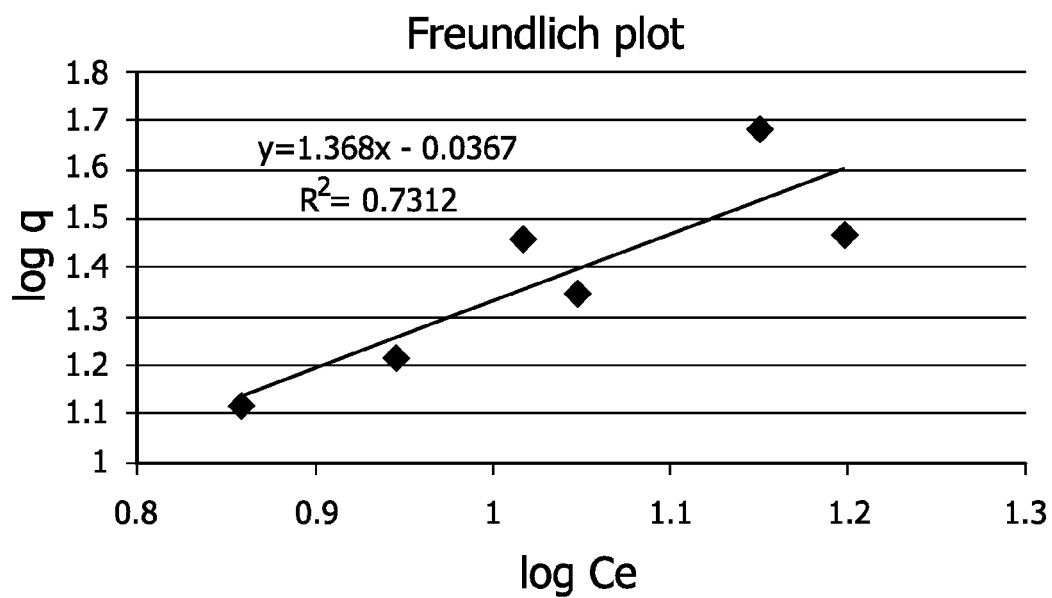
FIG. 3B illustrates a Freundlich isotherm model with adsorbent A2 (k=0.92 and n=0.73) (initial concentration of 17β-estradiol 100 ppb).

The Langmuir isotherm model was found to be better fit for the given results (FIG. 3).

The difference in the adsorption capacity of two different adsorbents A1 and A2 can be attributed to the use of two different crosslinking agents for the derivatization of the native β-CD. In the case of adsorbent A1, HMDI was used as crosslinking agent whereas EPI was used as crosslinking agent for the latter adsorbent. So, assuming that HMDI as crosslinking agent would give more efficient products, the method A1 was followed for further experiments.

Since the products obtained by following method A showed good results for the removal of estrogens in single and multicomponent systems, the products were prepared again following the same procedures as before to check the reproducibility of the products. Here, additional products were also prepared by changing the molar ratios of β-CD and the crosslinking agent (HMDI). Altogether, five different products were obtained which were tested for the removal of 17-β estradiol.

Adsorbent S2:
3.0 gm of β-CD was dissolved in 15 ml of DMSO. To this, 6 gm of silica was added and stirred at 60° C. for 15 min. To this solution, 3.2 ml HMDI was added dropwise and the mixture was left stirring 60° C. for 2 hrs. The mixture was then transferred to the oven at 60° C. for 18 hrs. A solid hard product was obtained which was crushed and sieved using mesh size 18×35. Thus obtained adsorbent was washed with MQ water and methanol and dried at 60° C. overnight under vacuum.

Adsorbent S3:
3.0 gm of β-CD was dissolved in 15 ml of DMSO. To this, 6 gm of silica was added and stirred at 60° C. for 15 min. To this solution, 6.4 ml HMDI was added dropwise and the mixture was left stirring 60° C. for 2 hrs. The mixture was then transferred to the oven at 60° C. for 18 hrs. A solid hard product was obtained which was crushed and sieved using mesh size 18×35. The adsorbent thus obtained was washed with MQ water and methanol and dried at 60° C. overnight under vacuum.

Adsorbent S4:
6.0 gm of β-CD was dissolved in 30 ml of DMSO. To this, 6 gm of silica was added and stirred at 60° C. for 15 min. To this solution, 6.4 ml HMDI was added dropwise and the mixture was left stirring 60° C. for 2 hrs. The mixture was then transferred to the oven at 60° C. for 18 hrs. A solid hard product was obtained which was crushed and sieved using mesh size 18×35. Thus obtained adsorbent was washed with MQ water and methanol and dried at 60° C. overnight under vacuum.

Adsorbent S5:
6.0 gm of β-CD was dissolved in 30 ml of DMSO. To this, 6 gm of silica was added and stirred at 60° C. for 15 min. To this solution, 12.8 ml HMDI was added dropwise and the mixture was left stirring 60° C. for 2 hrs. The mixture was then transferred to the oven at 60° C. for 18 hrs. A solid hard product was obtained which was crushed and sieved using mesh size 18×35. The adsorbent thus obtained was washed with MQ water and methanol and dried at 60° C. overnight under vacuum.

Adsorbent S6:
3.0 gm of β-CD was dissolved in 15 ml of DMSO. To this, 1.5 gm of silica was added and stirred at 60° C. for 15 min. To this solution, 6.4 ml HMDI was added dropwise and the mixture was left stirring 60° C. for 2 hrs. The mixture was then transferred to the oven at 60° C. for 18 hrs. A solid hard product was obtained which was crushed and sieved using mesh size 18×35. The adsorbent thus obtained was washed with MQ water and methanol and dried at 60° C. overnight under vacuum.

TABLE 4

Removal efficiencies of different adsorbents

| Product | Initial conc. (ppb) | Dosage (g/L) | Removal % |
|---|---|---|---|
| S2 | 25 | 0.6 | 62.3 |
| S3 | 25 | 0.6 | 22.2 |
| S4 | 25 | 0.6 | 94.4 |
| S5 | 25 | 0.6 | 90.2 |
| S6 | 25 | 0.6 | 25.5 |

Figure 4A:
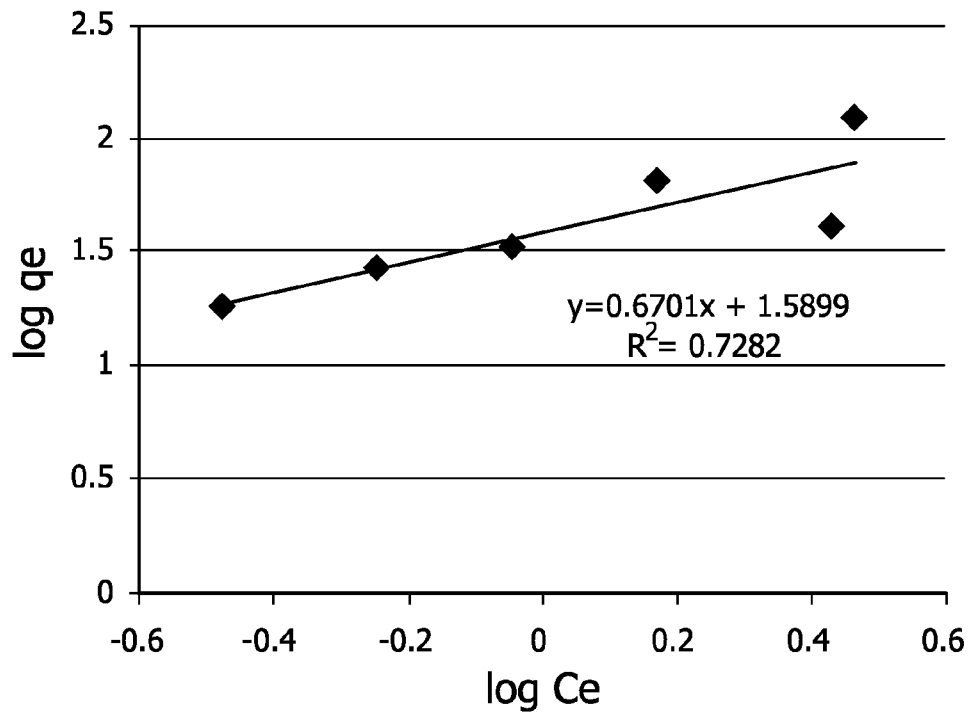
FIG. 4A illustrates a Freundlich isotherm model with adsorbent S5 (prepared with hexamethylene diisocyanate (HMDI) crosslinker; see Example 1) (initial concentration of 17β-estradiol 25 μg/L) (k=38.9 and n=14.9).
Figure 4B:
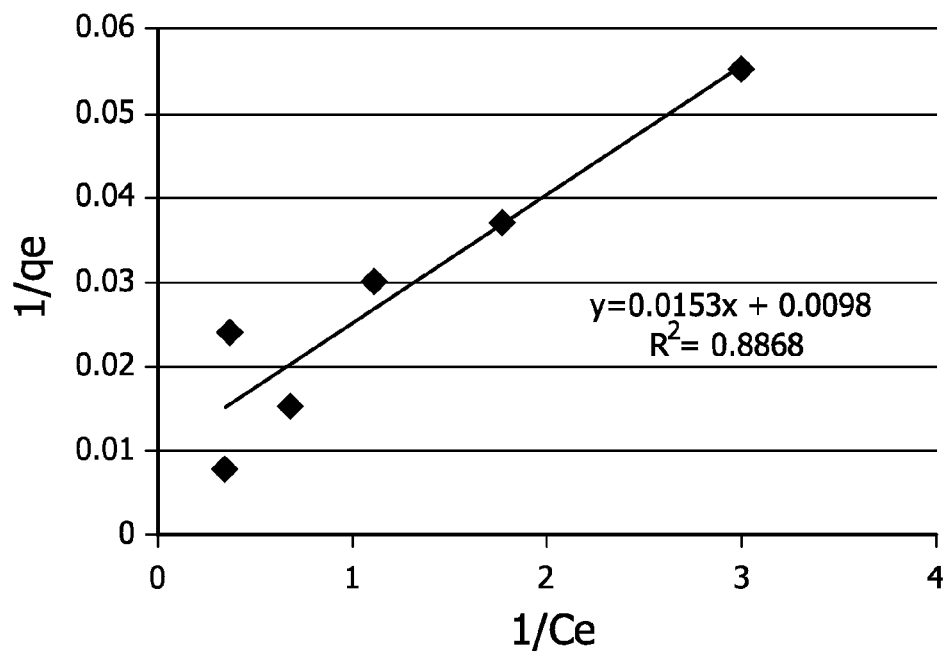
FIG. 4B illustrates a Langmuir isotherm model with adsorbent S5 (Qm=102 and b=0.64) (initial concentration of 17β-estradiol 25 μg/L).
Figure 5A:
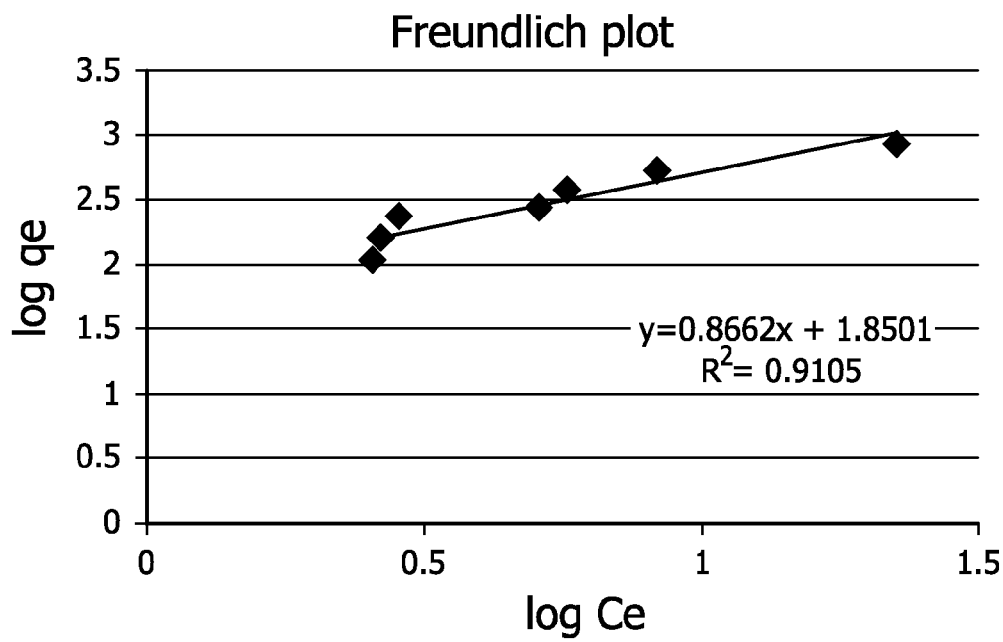
FIG. 5A illustrates a Freundlich isotherm model with adsorbent S5 (initial concentration of 17β-estradiol 100 μg/L) (k=70.8 and n=1.15).
Figure 5B:
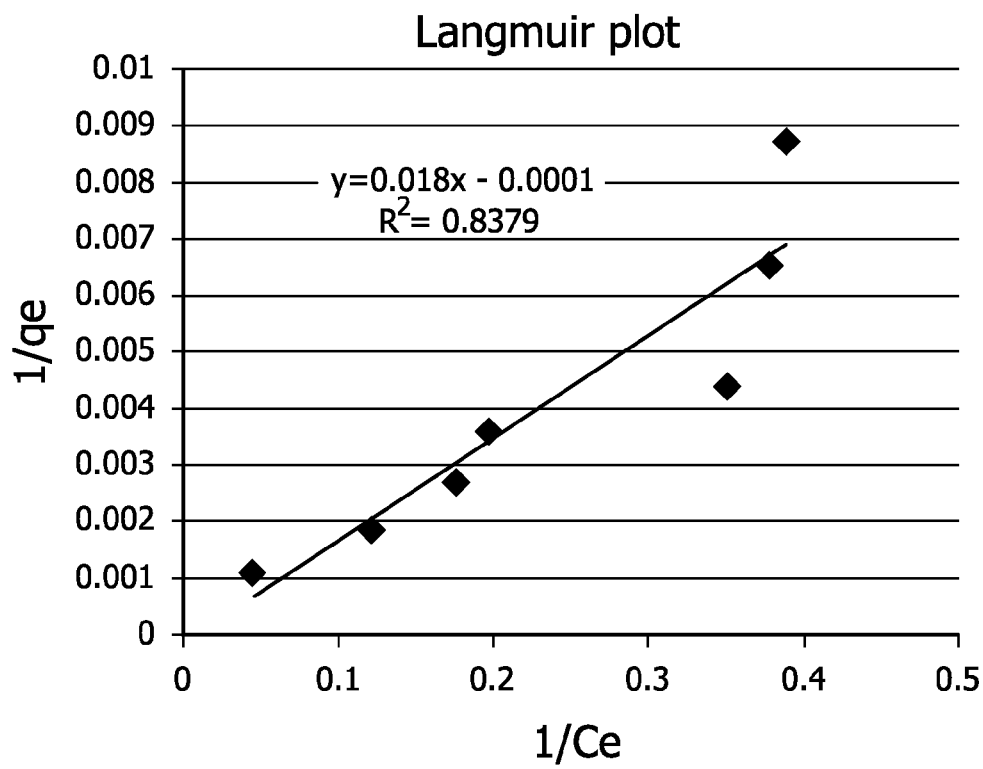
FIG. 5B illustrates a Langmuir isotherm model with adsorbent S5 (Qm=−1000 and b=−0.006) (initial concentration of 17β-estradiol 100 μg/L).

The above results show that the adsorption capacity of an adsorbent depends on the molar ratio of β-CD and the crosslinking agent used. From the results shown in Table 4, the best two adsorbents, S4 and S5, were chosen for the equilibrium studies. The results obtained from the new product S5 were consistent with the previous results for the removal of 17β-estradiol (Table 5 and FIGS. 4 and 5).

TABLE 5

Equilibrium studies with adsorbent S5 (initial con: 25 µg/L)

| Sample No. | Dosage (g/L) | Removal % |
|---|---|---|
| 1 | 0.2 | 89.4 |
| 2 | 0.4 | 94.6 |
| 3 | 0.6 | 90.2 |
| 4 | 0.8 | 96.7 |
| 5 | 1 | 97.9 |
| 6 | 1.5 | 98.7 |

Results for a Mixture of Estrogens and Progesterone

Figure 6:
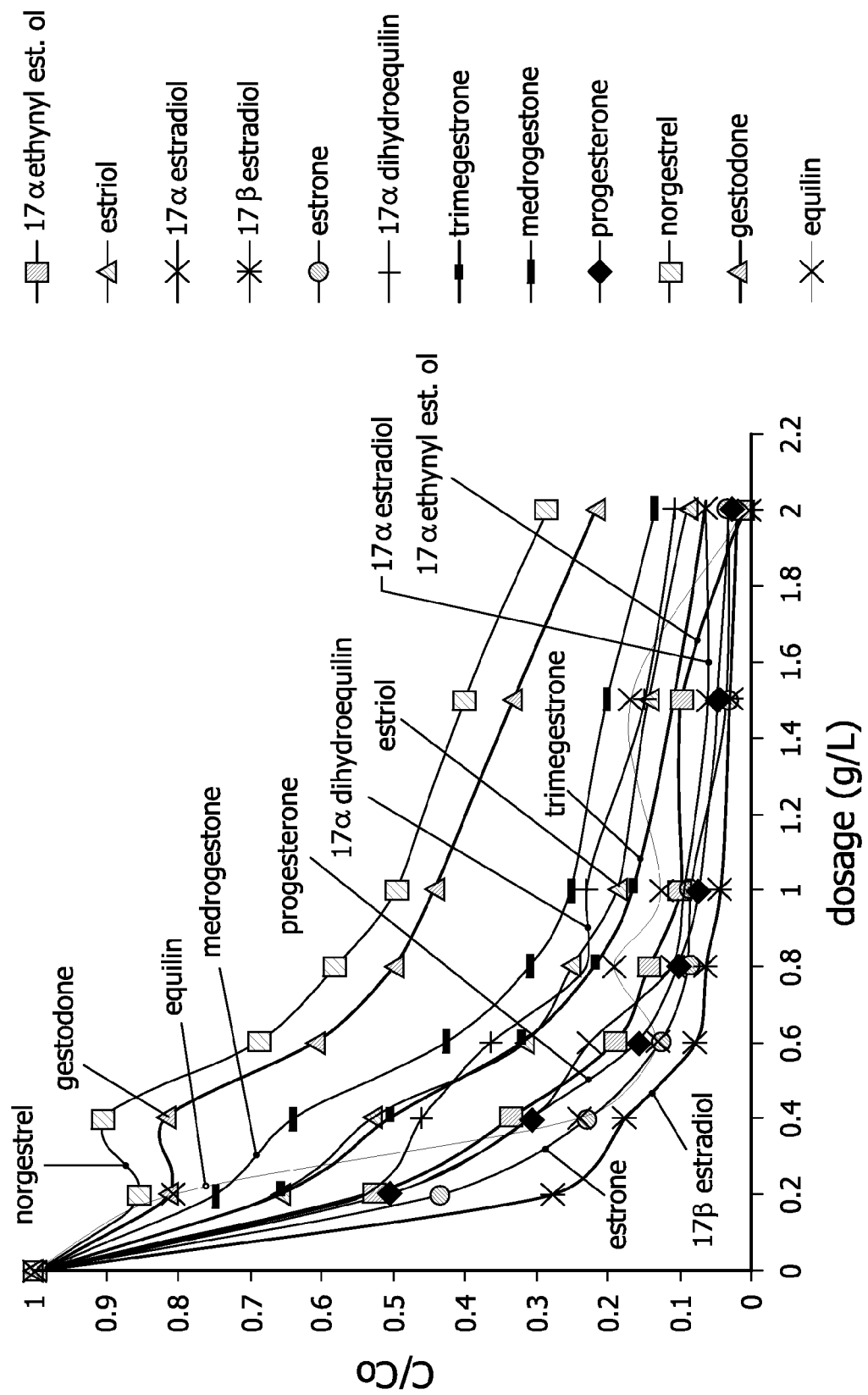
FIG. 6 illustrates removal of estrogens and progesterone in a multicomponent mixture with adsorbent S4 (prepared with hexamethylene diisocyanate (HMDI) crosslinker; see Example 1) (initial concentration each estrogen and progesterone 100 μg/L).
Figure 7:
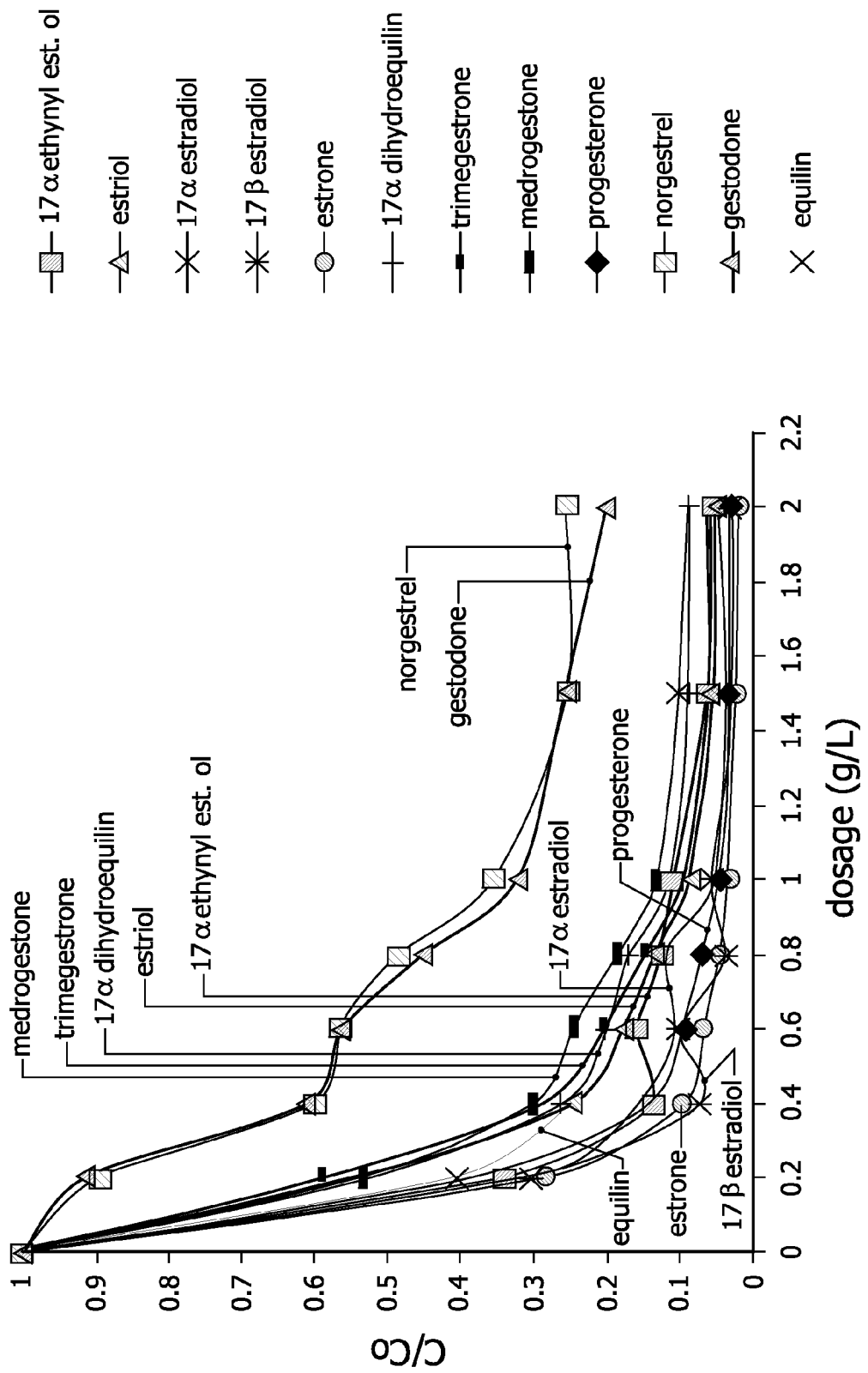
FIG. 7 illustrates removal of estrogens and progesterone in a multicomponent mixture with adsorbent S5 (initial concentration each estrogen and progesterone 100 μg/L).

The best adsorbents (S4 and S5) were tested for the removal of estrogens in multicomponent systems containing a mixture of 12 different steroid hormones comprising estrogens and progesterone: 17β-estradiol, 17α-ethynylestradiol, estriol, 17α-estradiol, estrone, 17α-dihydroequilin, trimegestrone, medrogestone, progesterone, norgestrel, gestodone, equilin. Both adsorbents S4 and S5 having 18-35 mesh size showed more than 90% removal for most of the estrogens from the estrogen mixture (FIGS. 6 and 7).

The experimental results in removing estrogens from both single component and multicomponent mixtures showed good removal of estrogens and progesterone. The removal of 17β estradiol was not affected by the introduction of other estrogens or progesterone in the mixture. Without wishing to be bound by any theory, this may be due to the high adsorption affinity of the adsorbent for 17β estradiol.

Additional adsorbents were synthesized by the same method as S4 in order to perform batch and column experiments. These adsorbents were named S4II (second batch) and S4III (third batch).

Figure 8:
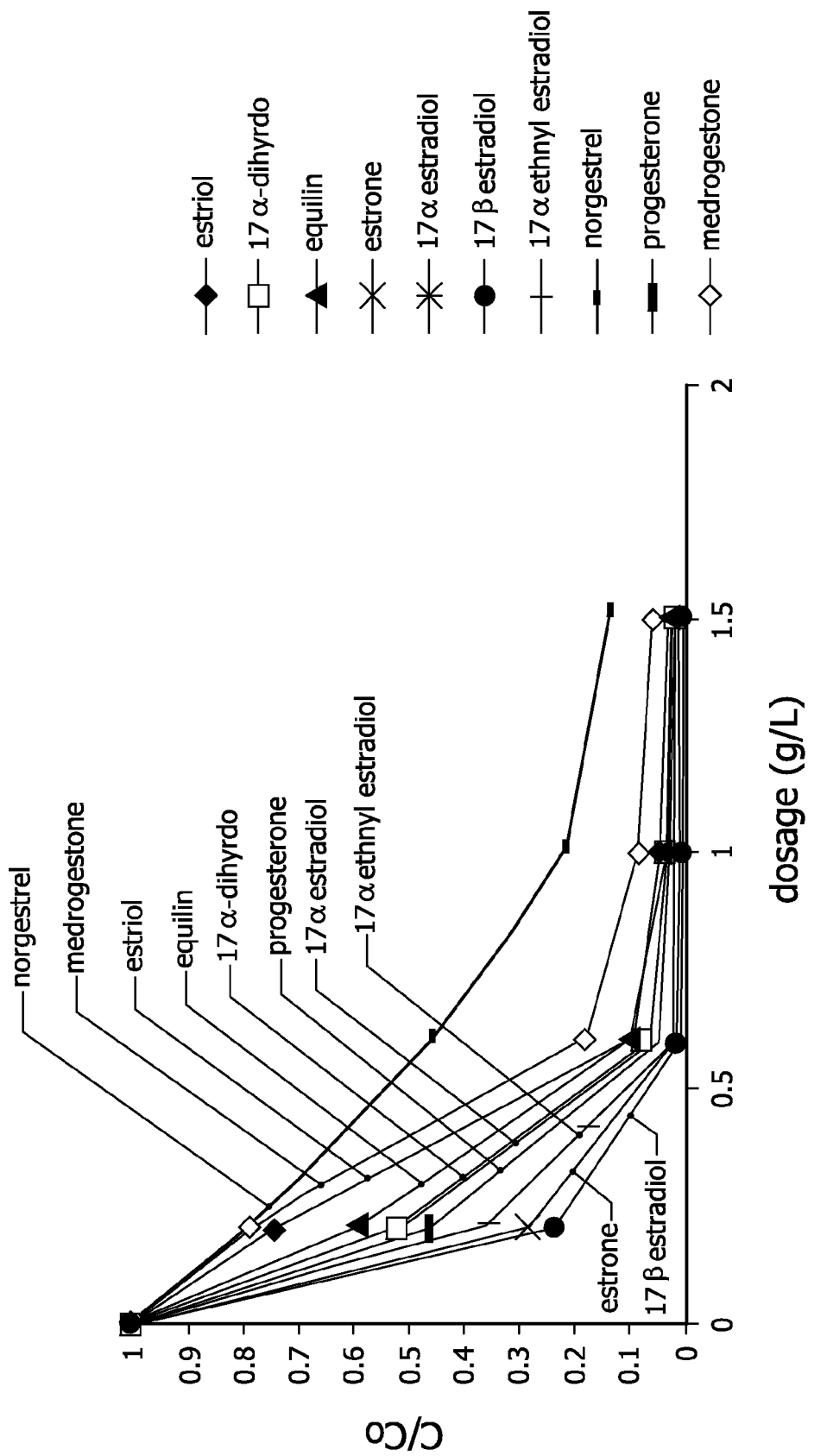
FIG. 8 illustrates removal of estrogens and progesterone in a multicomponent with adsorbent S4II (prepared with hexamethylene diisocyanate (HMDI) crosslinker; see Example 1) (initial concentration each estrogen and progesterone 100 μg/L).

Adsorbent S4II was tested for the removal of estrogens and progesterone in multicomponent systems containing a mixture of 10 different steroid hormones comprising estrogens and progesterone at an initial concentration of 100 μg/L of each estrogen or progesterone compound. The adsorbent showed very good results in removing more than 95% of most of the estrogens and progesterone present in the mixture (FIG. 8). As a control experiment, silica (40-100 mesh size) at a dosage of 1.5 g/L was also conducted but no significant removal of estrogens or progesterone was observed.

Once again, the experimental results in removing estrogens and progesterone from both single component and multicomponent mixtures showed good removal of estrogens and progesterone. The removal of 17β estradiol was not affected by the introduction of other estrogens in the mixture. Without wishing to be bound by any theory, this may be due to the high adsorption affinity of the adsorbent for 17β estradiol.

Effects of pH on the Removal of Estrogens and Progesterone

Figure 9:
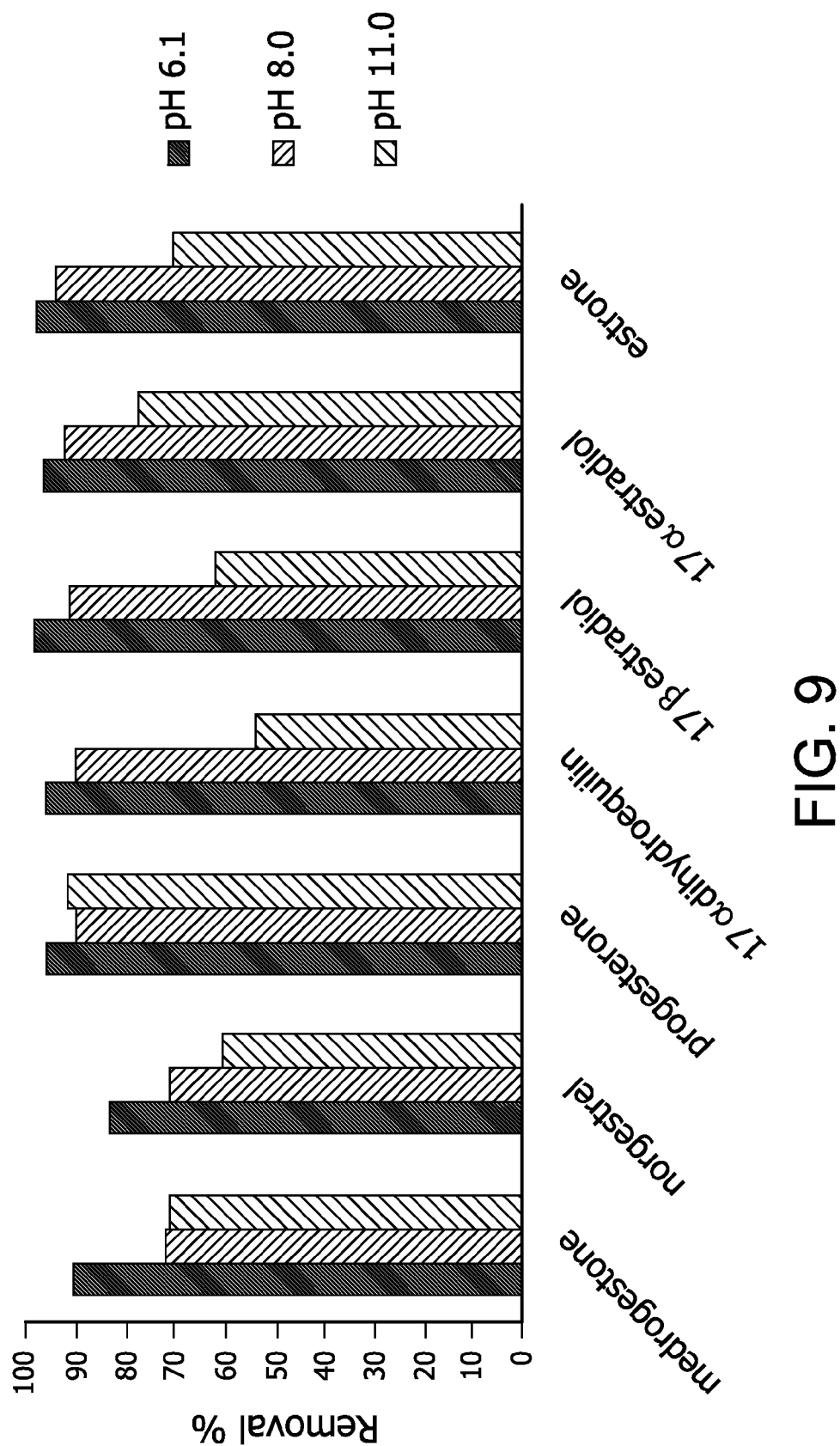
FIG. 9 illustrates the effects of pH on the removal of a mixture of steroid hormones. The concentration of each steroid hormone in the mixture was 100 μg/L. For each steroid hormone, the pH utilized from left to right on the bar graph was 6.1, 8.0 and 11.0.

To study the effects of pH on the removal of estrogens and progesterone in a mixture, three sets of batch experiments were conducted at pH 6, 8, and 11. The concentration of each estrogen or progesterone in the mixture was 100 μg/L. The results are shown in FIG. 9.

The results show that the adsorption capacity of the adsorbent decreases as the pH increases from 6.1 to 8.0 to 11.0. Without wishing to be bound by any theory, this may be because the pH of the water influences the structure of the contaminants or the structure of the β-CD itself. Certain estrogens, such as medrogestone, norgestrel, and progesterone were not affected significantly by the changes in pH. The reason may be attributed to the structures of these compounds which do not have pKa values.

Example 2: Equilibrium Studies with PFOA

Results for PFOA

Figure 10:
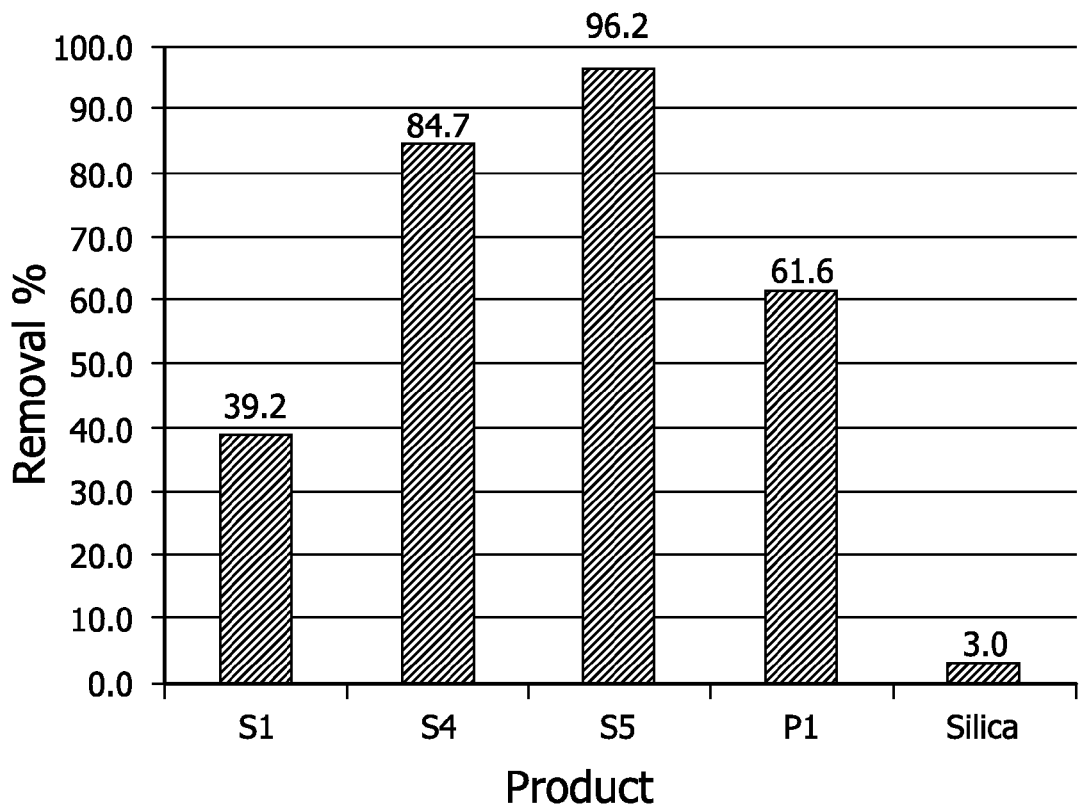
FIG. 10 illustrates removal of PFOA (perfluorooctanoic acid) using different adsorbents and silica (Initial concentration PFOA 25 μg/L; dosage: 1.5 g/L; contact time: 48 hrs).

All the products obtained by the modification of native β-cyclodextrin were tested for the removal PFOA in MQ water at an initial concentration of 25 μg/L, with a sample volume of 400 ml and a reaction time of 48 hours. A 10 ml sample was collected into a clean glass vial and 10 μL of internal standard was added and vortexed. The sample was then directly injected into LC/MS/MS for analysis. The screening showed that the products S4 and S5 are efficient in removing PFOA from the given system (Table 7 and FIG. 10).

TABLE 7

Screening results for the removal of PFOA

| Sample No. | Product | Dosage, g/L | Removal % |
|---|---|---|---|
| 1 | S1 | 1.5 | 39.24758 |
| 2 | S4 | 1.5 | 84.70511 |
| 3 | S5 | 1.5 | 96.17053 |
| 4 | P1 | 1.5 | 61.63299 |
| 5 | Silica | 1.5 | 2.960407 |

Equilibrium Studies with Adsorbent S5

From the screening results, the best adsorbent S5 was chosen for the equilibrium studies with PFOA at an initial concentration of 25 μg/L, with a sample volume of 400 ml and a reaction time of 48 hours. The initial pH of the solution with PFOA was 5.67. It was observed that more than 99% removal of PFOA occurred, and there was not much change in the pH of initial and final solutions (Table 8). No significant removal of PFOA was observed in case of silica.

TABLE 8

Equilibrium studies with adsorbent S5 (direct injection)

| | Sample No. | Dosage (g/L) | Removal % | Final pH |
|---|---|---|---|---|
| | Blank | | | 6.88 |
| Adsorbent S5 | 1 | 0.2 | 98.63011 | 6.13 |
| | 2 | 0.4 | 99.04706 | 6.07 |
| | 3 | 0.6 | 99.62431 | 5.83 |
| | 4 | 0.8 | 99.72323 | 5.61 |
| | 5 | 1 | 99.78674 | 5.57 |
| | 6 | 1.5 | 99.6367 | 5.65 |
| | 7 | 2 | 99.71427 | 5.44 |
| Silica | 8 | 1.5 | −0.288 | 5.58 |

Figure 11:
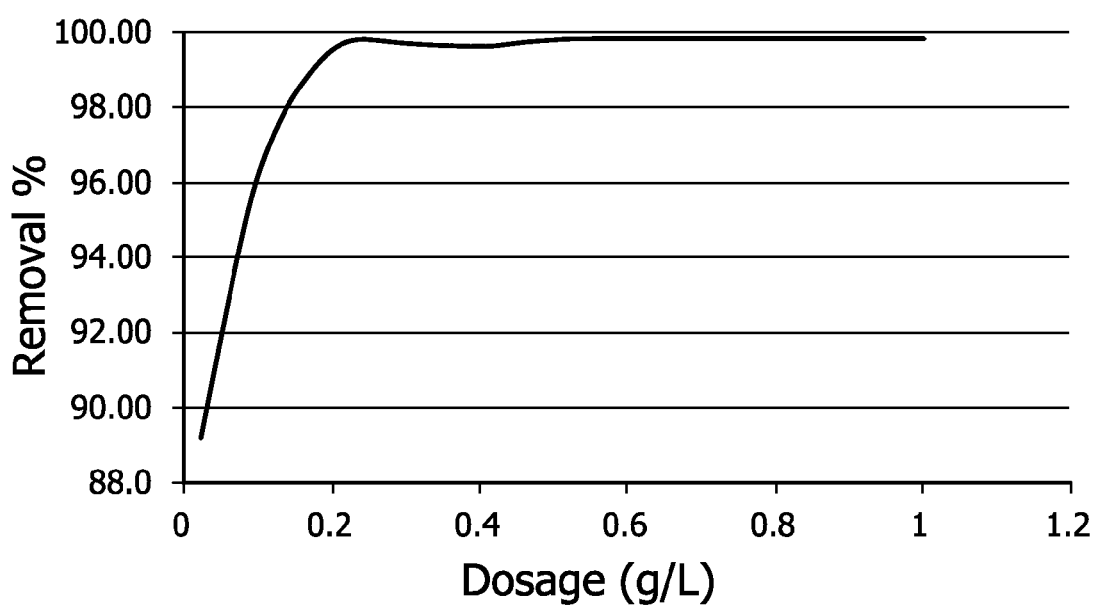
FIG. 11 illustrates removal of PFOA with adsorbent S5 (Initial concentration PFOA 25 μg/L; sample volume: 200 mL; contact time: 48 hrs).
Figure 12A:
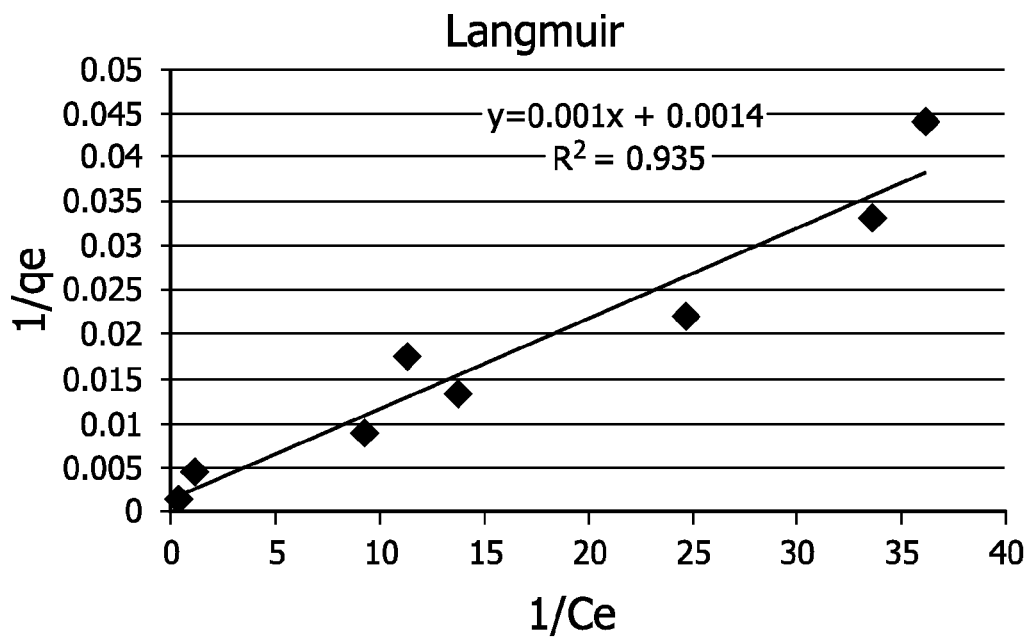
FIG. 12A illustrates a Langmuir isotherm model with adsorbent S5 (initial concentration PFOA 100 μg/L) (Qm=714 and b-1.4).
Figure 12B:
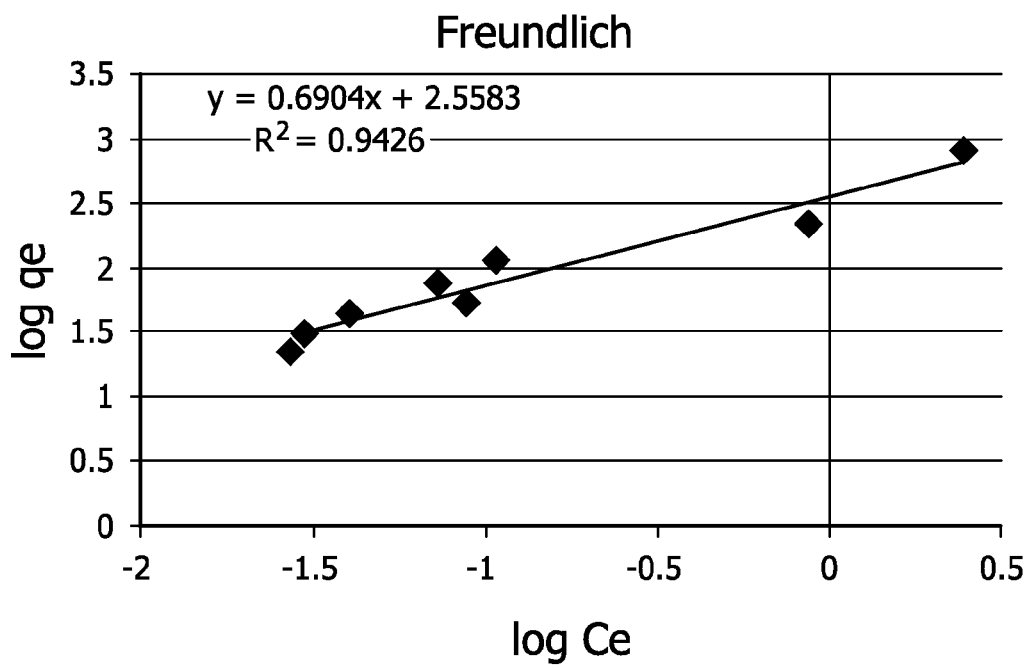
FIG. 12B illustrates a Freundlich isotherm model with adsorbent S5 (k=361.6 and n=1.45) (initial concentration PFOA 100 μg/L).

As the maximum removal of PFOA was below the detection limit (0.25 ppb), another experiment was done with solid phase extraction to analyze samples to lower detection limits. The results are shown in FIGS. 11 and 12.

Equilibrium Studies with Other Products

Figure 13:
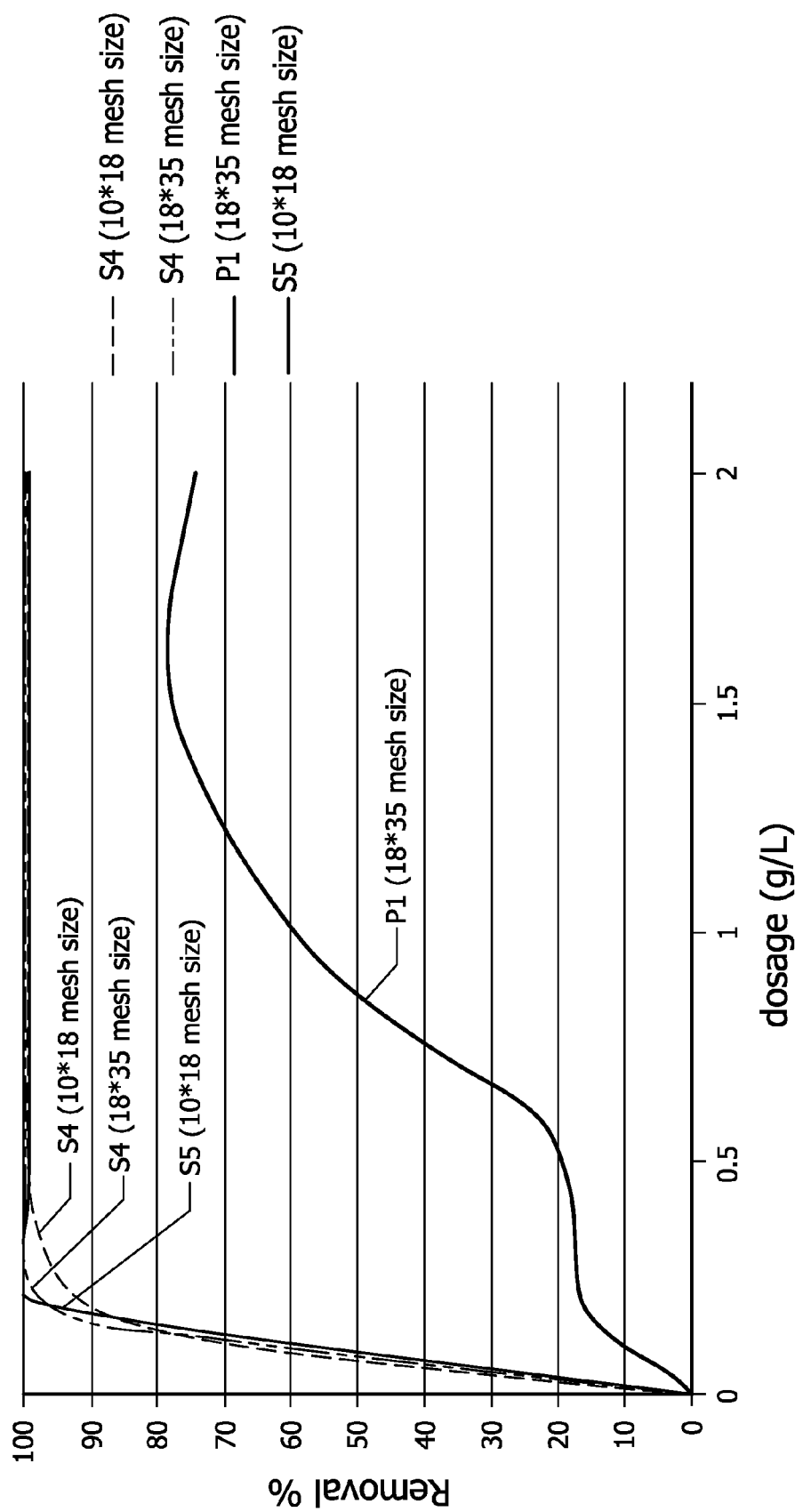
FIG. 13 illustrates equilibrium studies for the removal of PFOA with different adsorbents: S4 (10×18 mesh size), S4 (18×35 mesh size), P1 (18×35 mesh size) and S5 (18×35 mesh size) (initial concentration PFOA 25 μg/L; sample volume: 400 mL; contact time: 48 hrs).

Further equilibrium experiments were also conducted with other products and different mesh sizes of the same product. The results showed that the products S4 and S5 follow similar trends in the removal of PFOA. One more set of equilibrium studies was done with product S4 but having two different mesh sizes (10×18 and 18×35) to see the effects of particle size in the removal of PFOA. The results show similar trends in the removal despite having different mesh sizes (FIG. 13).

Results for a Mixture of Perfluorocarbons

Figure 14:
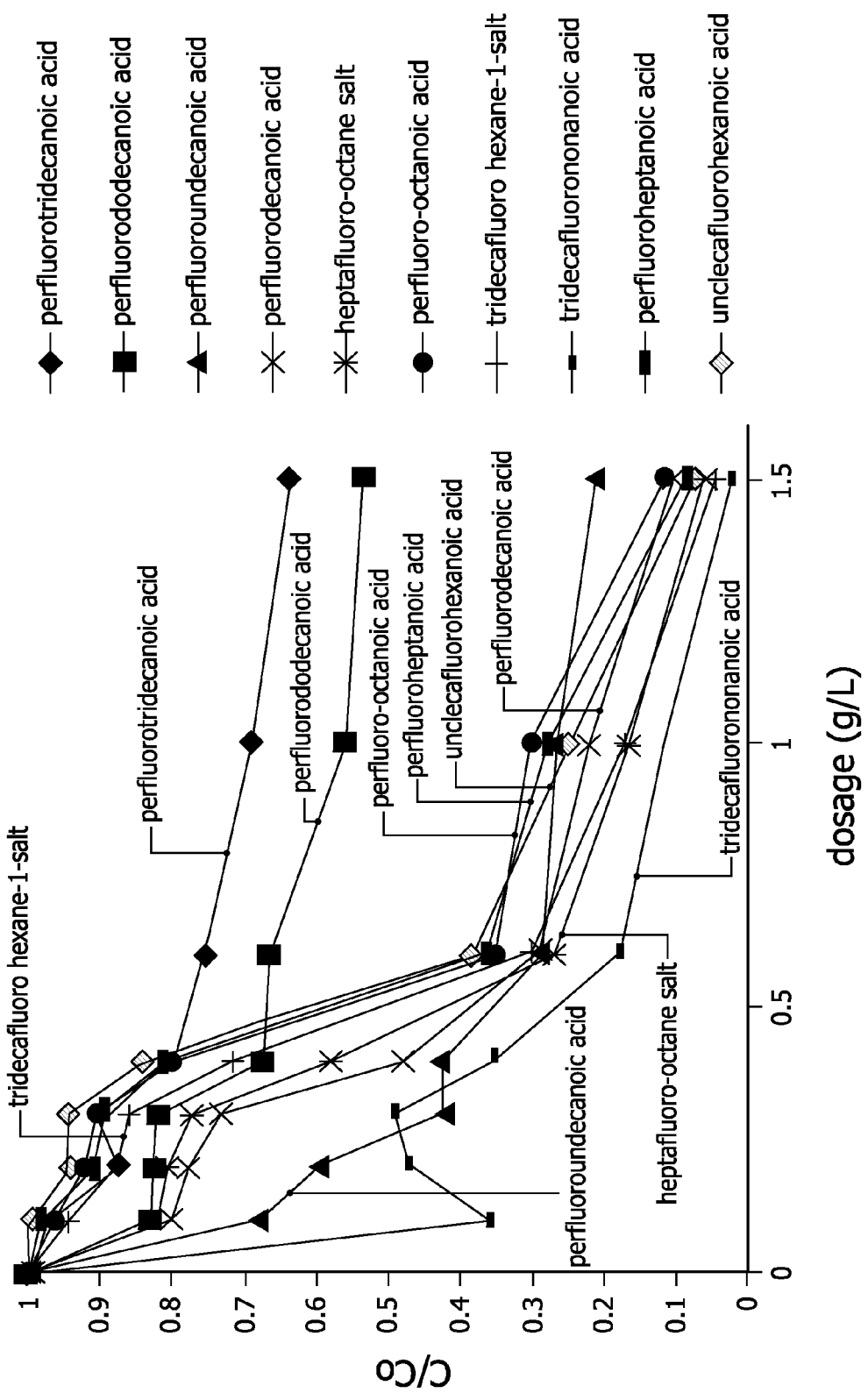
FIG. 14 illustrates removal of perfluorocarbons with adsorbent S4II (initial concentration of each perfluorocarbon 50 μg/L; contact time 48 hours).

As discussed supra, the adsorbent S4II was very efficient at removing estrogens from water. Therefore, adsorbent S4II was used to conduct a batch experiment with a mixture of 10 PFCs. The adsorbent was successful in removing most of the PFCs (FIG. 14). No significant removal was observed with silica at 1.5 g/L. The adsorbent removed over 99% PFOA at an adsorbent dosage of 0.2 g/L in a single component system. In a multicomponent system, the removal of PFOA was 90% at 1.5 g/L of adsorbent dosage. This indicates that the adsorbent has a high affinity for other PFCs such as tridecafluorononanoic acid, heptafluorooctane salt, and tridecafluoro hexane-1-salt. Certain PFCs such as perfluorotridecanoic acid and perfluorododecanoic acid showed very low removal compared to other PFCs. Without wishing to be bound by any theory, the reason may be attributed to the structure of these compounds which represent the longest-chained molecules in the mixture.

Example 3: Equilibrium Studies with Bisphenol A (BPA)

Batch Experiments with BPA

The adsorption equilibrium studies with another adsorbent S4II was carried out for the removal of BPA at an initial concentration of 50 mg/L. At the same time, the removal efficiency of the adsorbent was also compared with silica (40-100 mesh size) at a given dosage.

Figure 15:
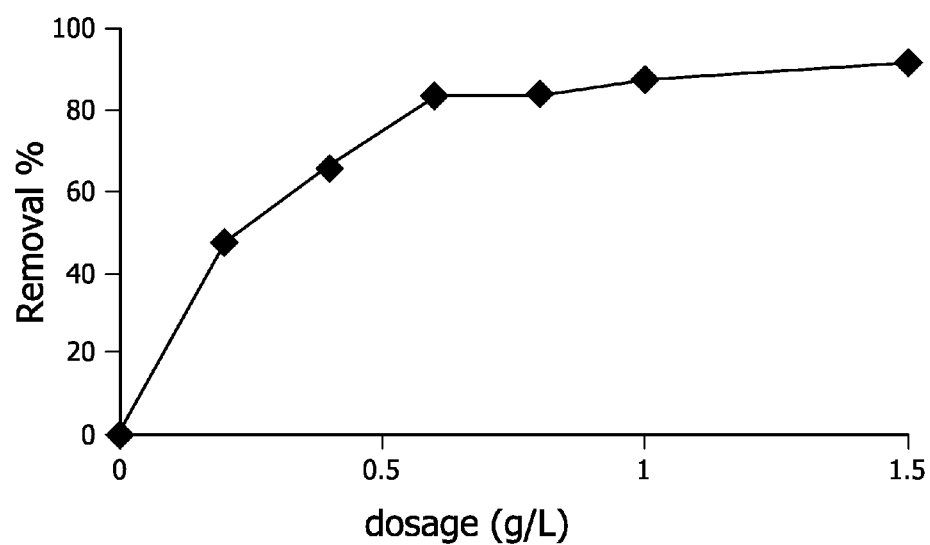
FIG. 15 illustrates removal of bisphenol A (BPA) with adsorbent S4II (initial concentration BPA 50 μg/L; contact time 48 hours).
Figure 16A:
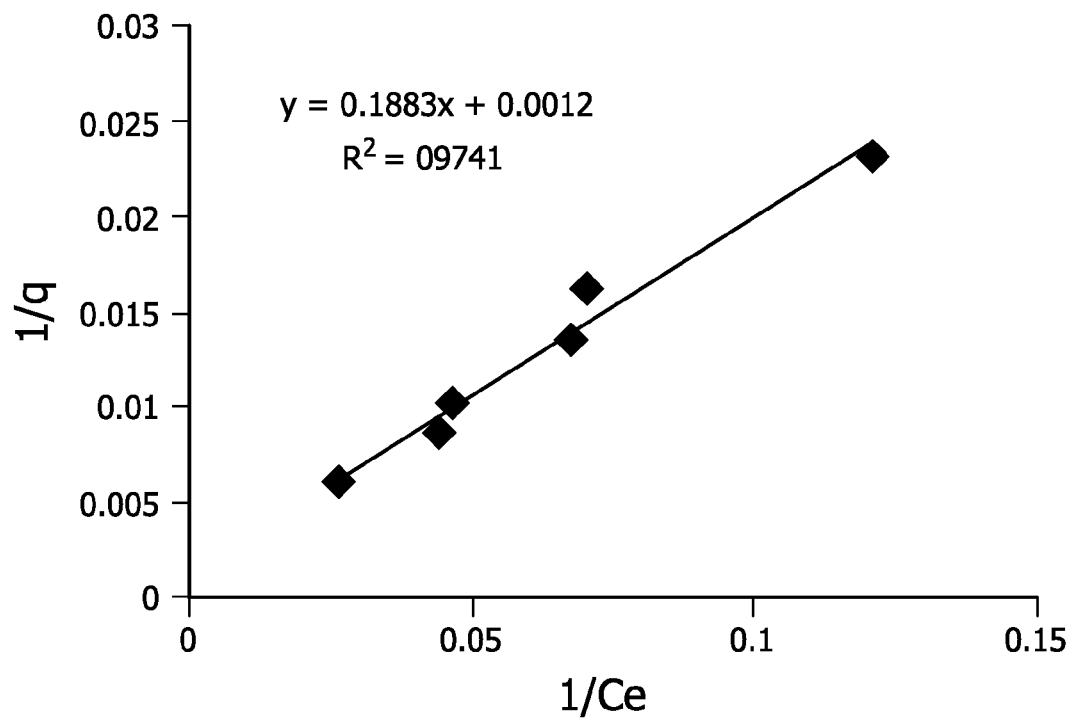
FIG. 16A illustrates a Langmuir isotherm model with adsorbent S4II (initial concentration BPA 100 μg/L).
Figure 16B:
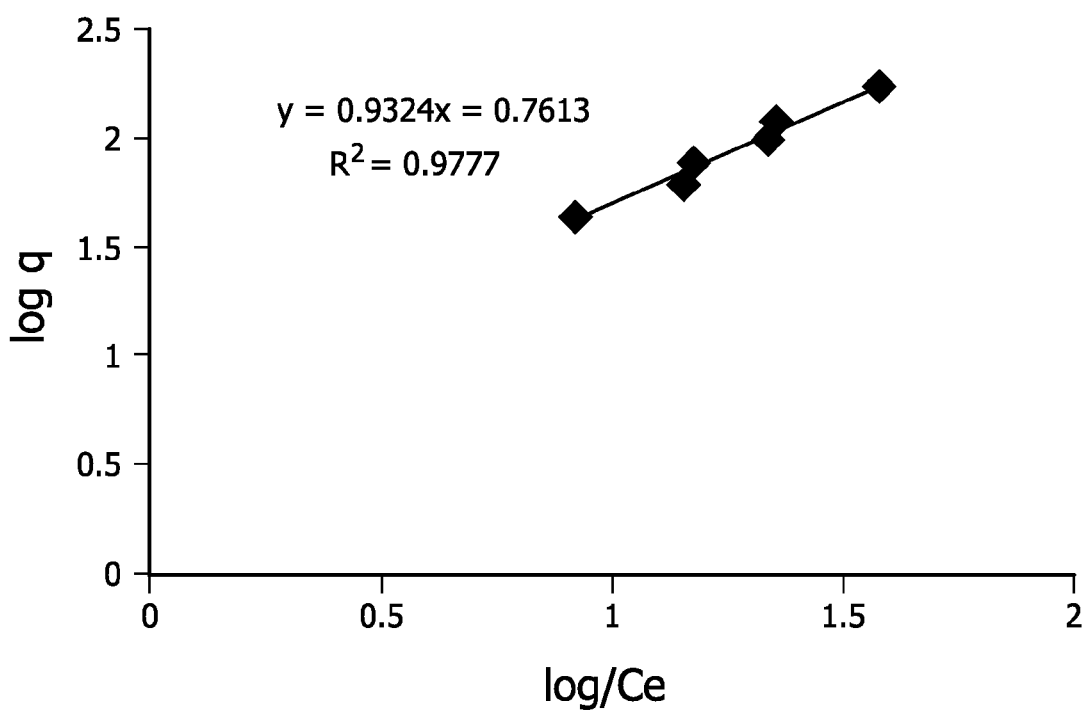
FIG. 16B illustrates a Freundlich isotherm model with adsorbent S4II (initial concentration BPA 100 μg/L).

The equilibrium studies showed that at a dosage of 1.5 g/L, maximum removal of 91% was observed (FIG. 15). On the other hand, no significant removal was observed with silica as an adsorbent. The obtained data were fitted to both Langmuir and Freundlich isotherm models which are shown in FIG. 16.

The removal of BPA with the adsorbent can be attributed to the formation of inclusion complexes with β-CD molecules. However, the adsorbent showed less affinity for BPA than for estrogens and PFOA.

Effect of pH

Figure 17:
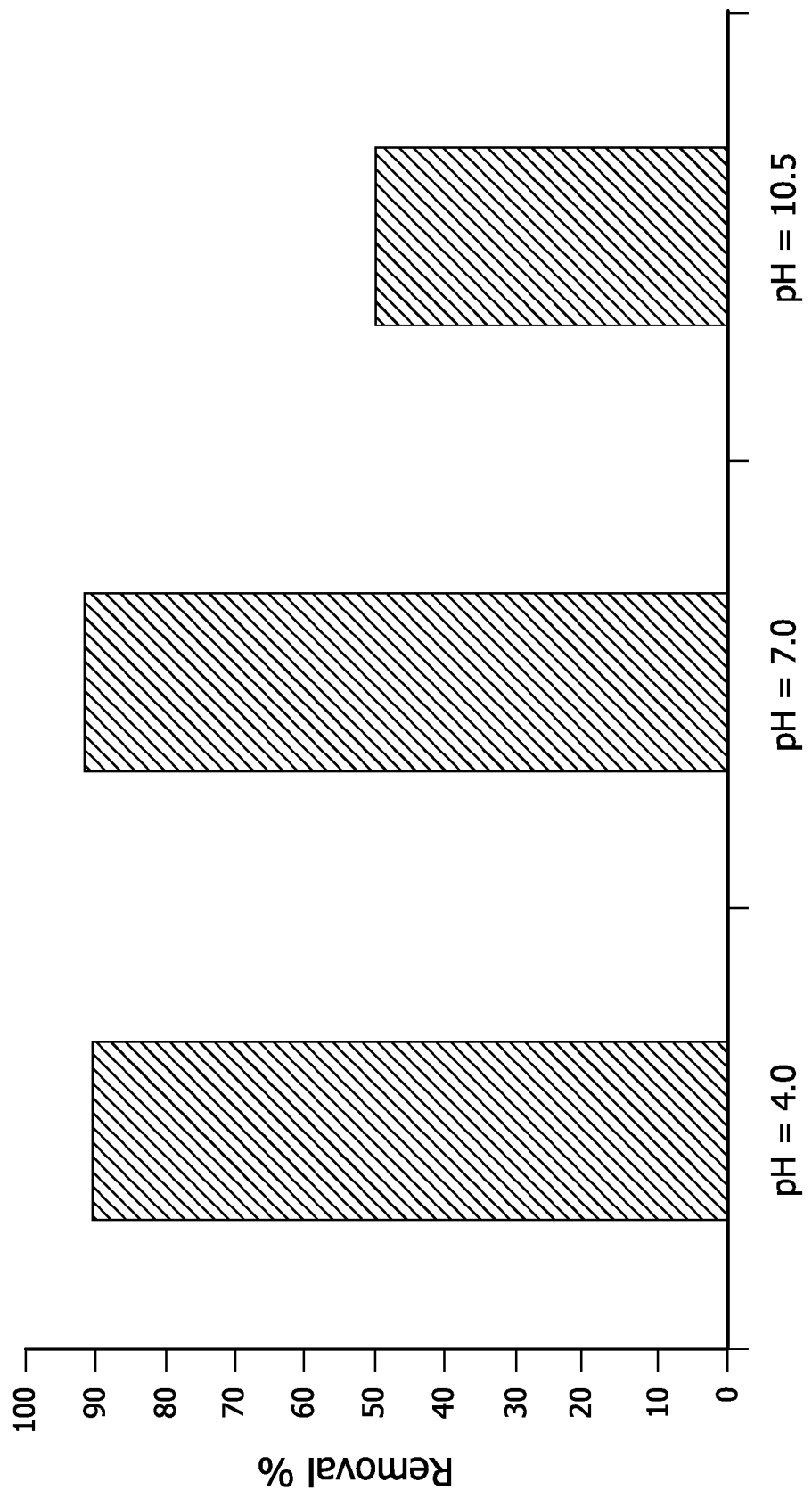
FIG. 17 illustrates the effect of pH on the removal of BPA with adsorbent S4II (initial concentration BPA 50 μg/L; contact time 48 hours; adsorbent dosage 1.5 g/L).

In order to study the effect of pH on the removal of BPA, three different pH conditions were used: pH 4.0, 7.0 and 10.5. The equilibrium experiment was conducted at 1.5 g/L of adsorbent dosage. The initial concentration of BPA was 100 mg/L. The results are shown in FIG. 17.

It was observed that the removal of BPA remained the same in acidic and neutral pH. But, at pH 10.5, which also represents the pKa for BPA, the removal of BPA decreased from 90% to 50%.

Comparison of Twelve Adsorbents for Removal of PFOA, BPA and 17β Estradiol

Twelve different adsorbents prepared as described supra were tested for the removal of 17β estradiol, PFOA and BPA under batch conditions (in MQ water). The following experimental conditions were employed:

Initial Concentration:

| | |
|---|---|
| Bisphenol A (BPA) | 100 μg/L |
| Perfluorooctanoic acid (PFOA) | 50 μg/L |
| 17β estradiol | 25 μg/L |
| Adsorbent dosage | 1.5 g/L |
| Contact time | 48 hrs |
| Temperature | 293 K |
| Initial pH | 5.7-6.5 |

The results are summarized in Table 9.

TABLE 9

Removal of 17β estradiol, PFOA and BPA

| | Removal % | | |
|---|---|---|---|
| Adsorbents | PFOA | BPA | *17β estradiol |
| A1 | 96.7 | 95.2 | 94 |
| A2 | 98.6 | 86.8 | 72 |
| A3 | 80.4 | 64.6 | 59 |
| B1 | 3.1 | 18.5 | 46 |
| B2 | −1.8 | 11.6 | 43 |
| B3 | −0.4 | 31.2 | 12 |
| B4 | −1.7 | 12.3 | 11 |
| B5 | 2.4 | 24.6 | 28 |
| C1 | 1.2 | 23.7 | 47 |
| C2 | 78.7 | 32.7 | 48 |
| C3 | 98.2 | 61.1 | 69 |
| C4 | 2.8 | 30.1 | 58 |

Example 4: Column Experiments with Estrogens and Progesterone

Column Design

For column experiments, a column with 2.5 cm internal diameter and 30 cm long was used. With the empty bed contact time of 1 min and the velocity of 5 m/hr, the other design parameters were calculated such as flow rate (41 ml/min), weight of the adsorbent (24.5 g), and bed depth (8 cm). Before performing column experiments, the column was conditioned with MQ water for 15 hrs.

Results with Estrogen and Progesterone Mixture

Figure 18A:
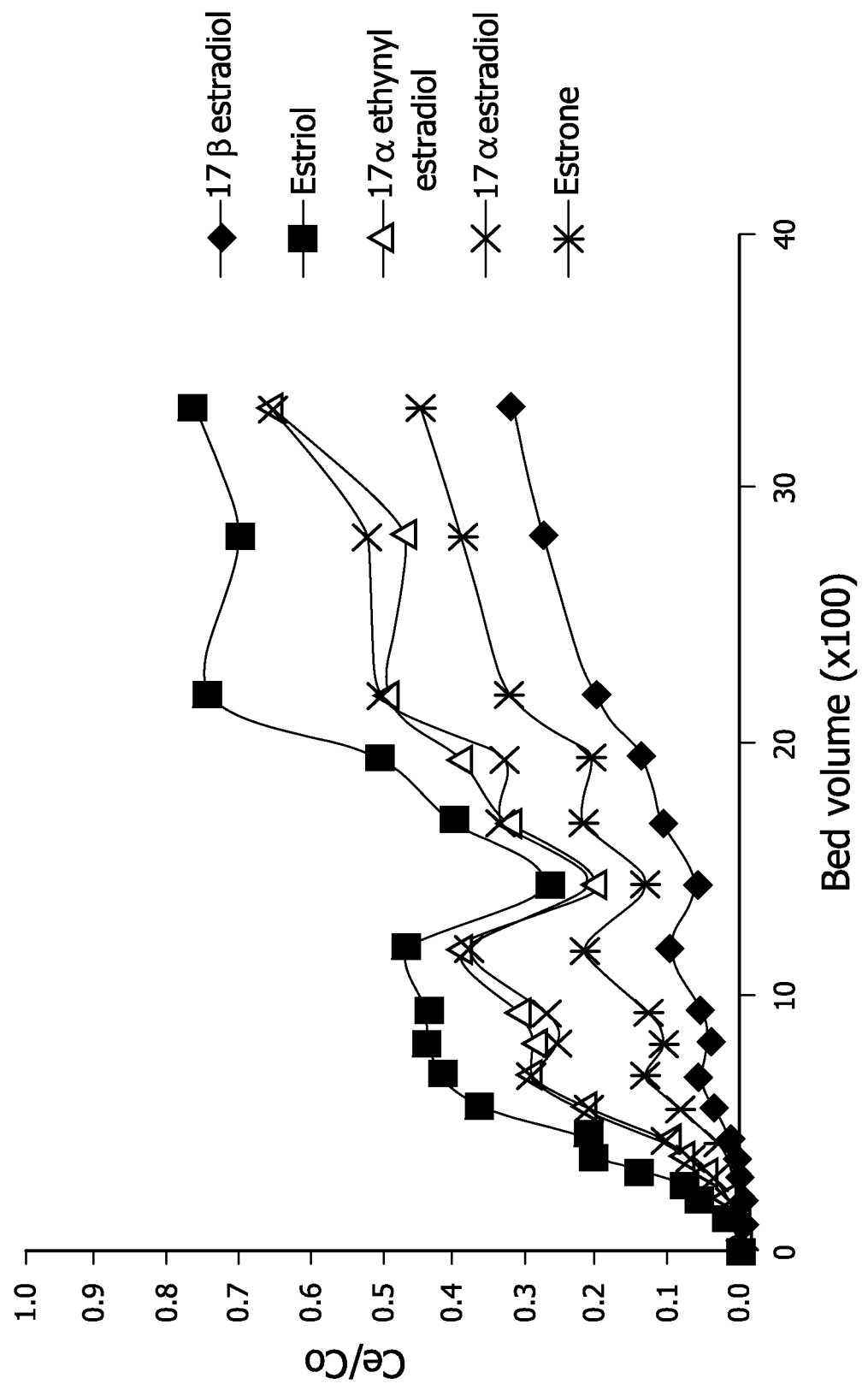
FIG. 18A illustrates removal of estrogens from a column experiment with adsorbent S4II (initial concentration of each estrogen 100 μg/L).
Figure 18B:
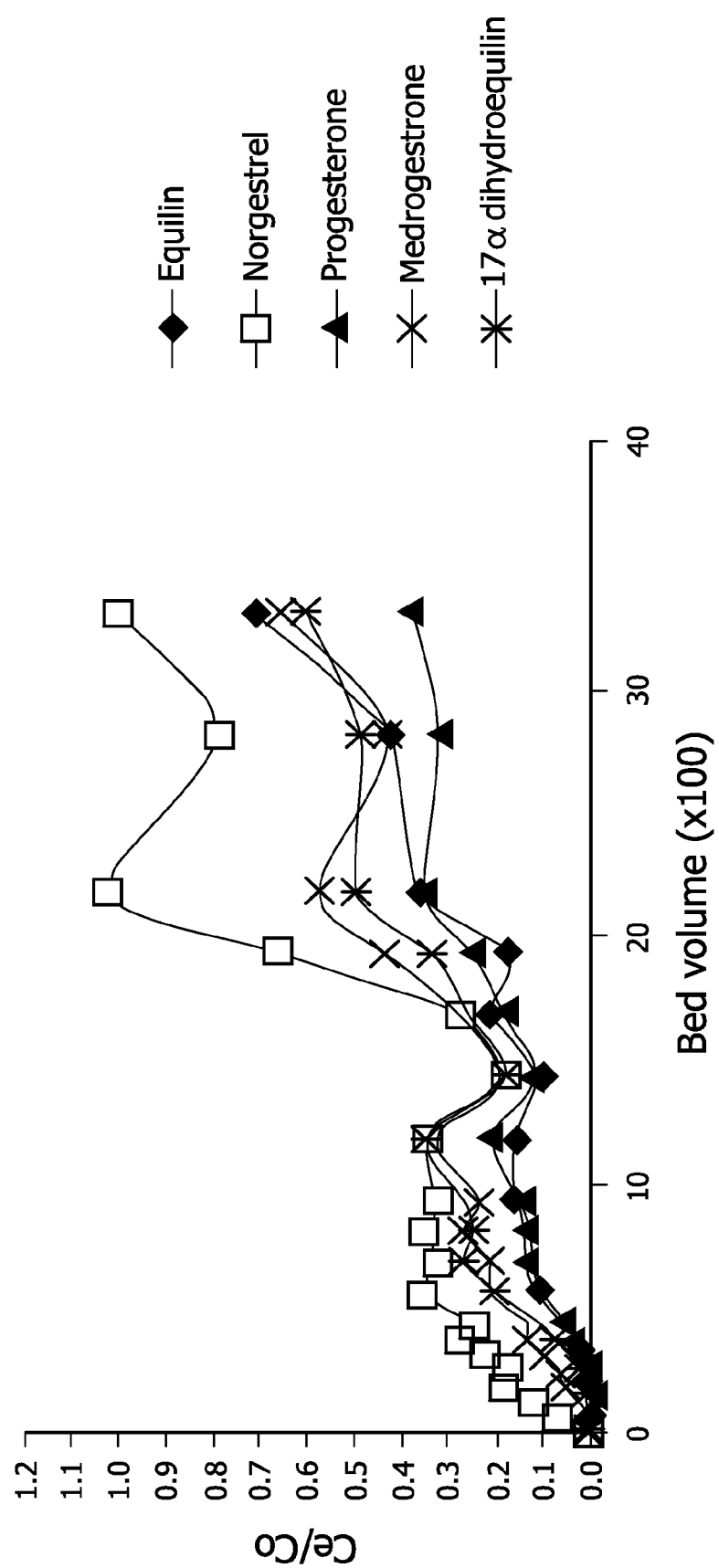
FIG. 18B illustrates removal of progesterones from a column experiment with adsorbent S4II (initial concentration of each estrogen 100 μg/L).

For column experiments, adsorbents S4II and S4III were prepared in bulk quantity following the same procedures as mentioned earlier. The column experiments were conducted at an initial concentration of 100 mg/L of each steroid hormone in a mixture of ten steroid hormones comprising estrogens and progesterone. The column packed with the adsorbent was continuously fed with the estrogens and progesterone working solution in MQ water. The inlet (Co) and outlet (Ce) samples were analyzed at regular intervals and the results are shown in FIG. 18.

Figure 19A:
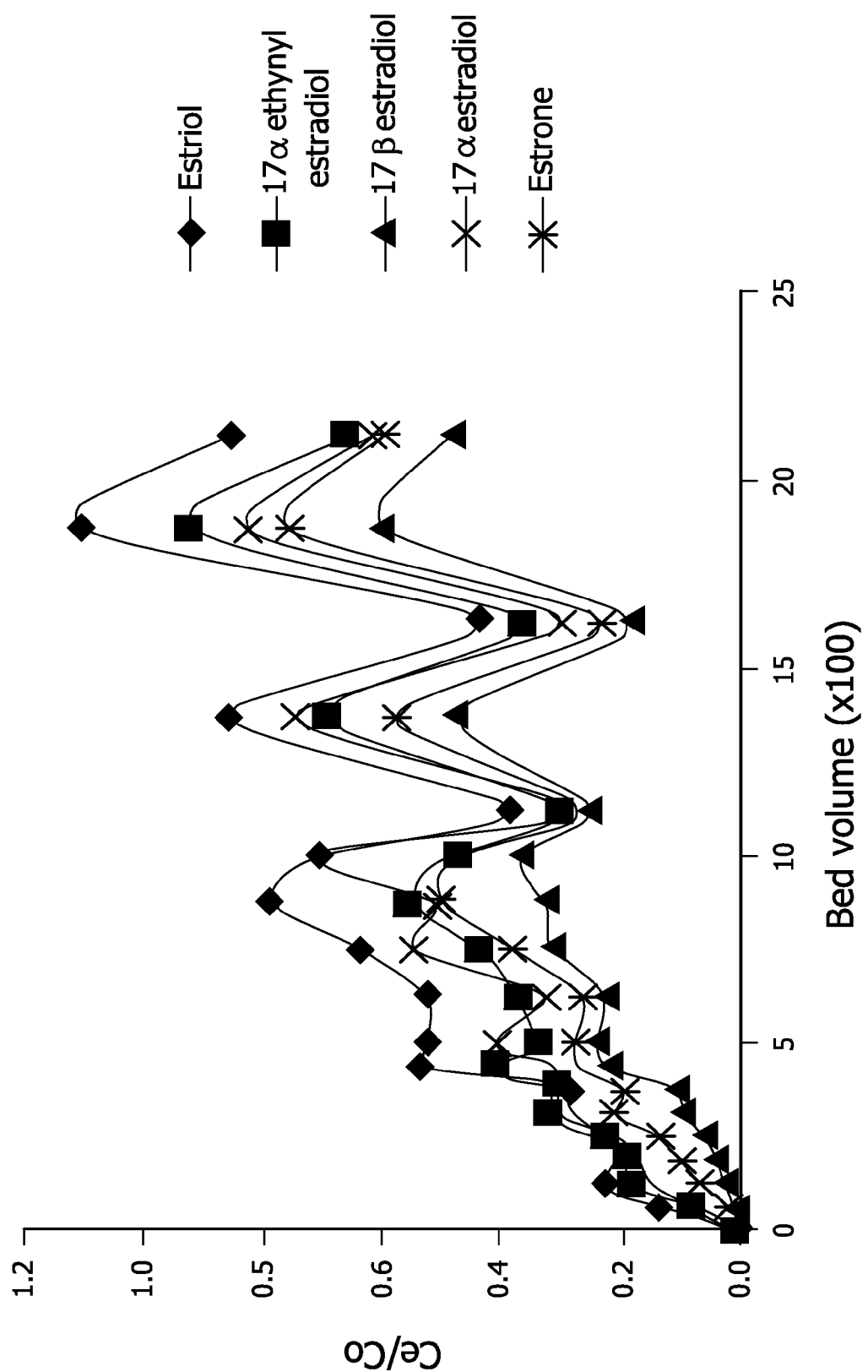
FIG. 19A illustrates removal of estrogens (estriol, 17α ethynyl estradiol, 17β estradiol, 17α estradiol and estrone) from a column experiment with adsorbent S4III (prepared with hexamethylene diisocyanate (HMDI) crosslinker; see Example 1) (initial concentration of each estrogen 100 μg/L).
Figure 19B:
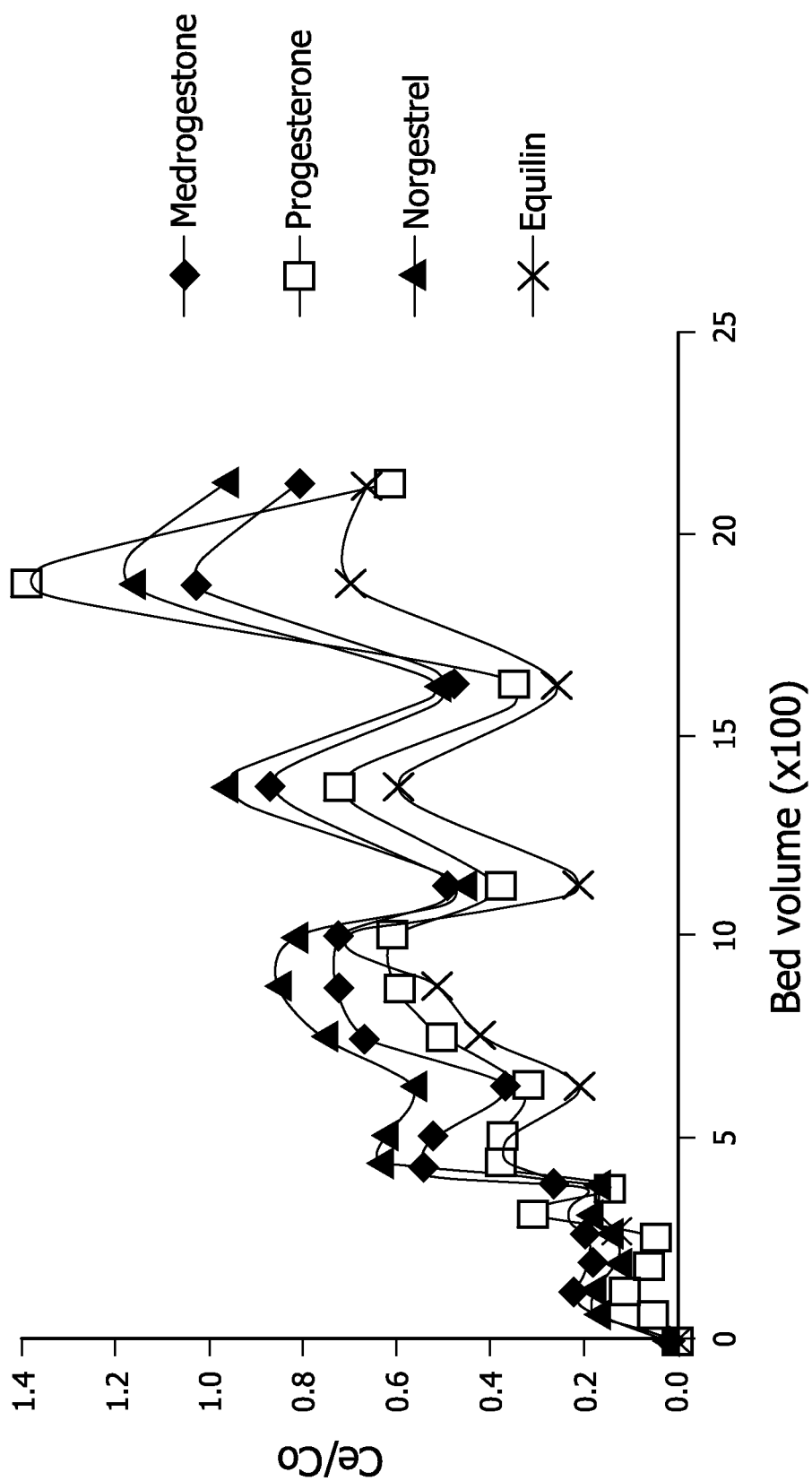
FIG. 19B illustrates removal of progesterones (medrogestone, progesterone and norgestrel) and an estrogen (equilin) from a column experiment with adsorbent S4III (initial concentration of each steroid hormone 100 μg/L).

A column experiment was also conducted using adsorbent S4III. The same column design parameters were used as in the case of adsorbent S4II. The results from this column experiment are shown in FIG. 19.

In batch experiments, the adsorbent S4III was found to be very effective in removing estrogens, progesterone, PFCs and BPA in MQ water systems. The same adsorbent showed very good results in column experiments as well. The adsorbent S4III was found to be less effective in removing estrogens and progesterone as compared to adsorbent S4II based on column experimental results. However, in both cases, the removal of estrogens showed a similar pattern where both adsorbents showed a high removal of estrogens such as 17β-estradiol and estrone.

Example 5: Column Experiments with BPA

Results

Figure 20:
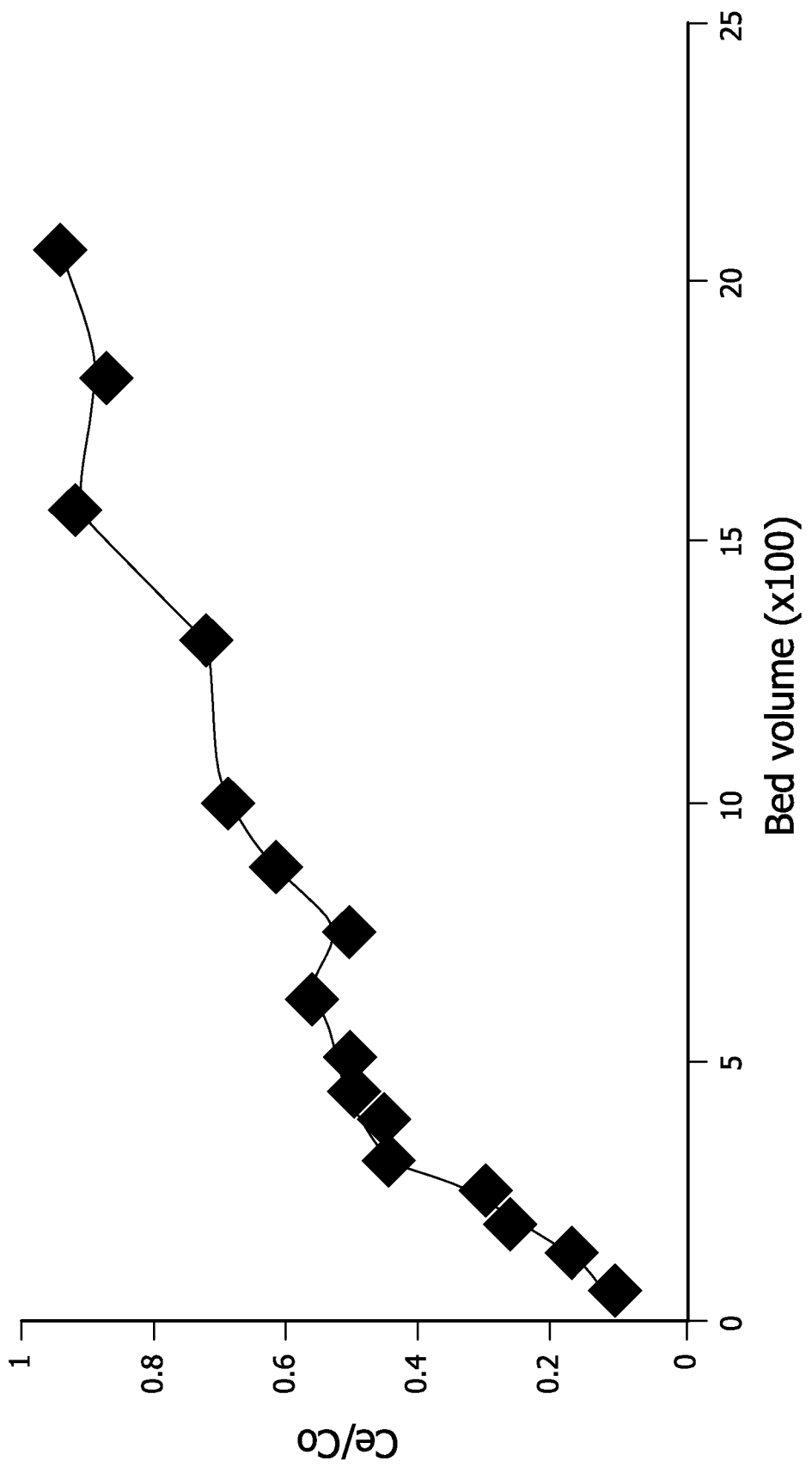
FIG. 20 illustrates removal of BPA from column experiment with Adsorbent S4III.

Adsorbent S4III was used to conduct column experiments with BPA at an initial concentration of 100 μg/L. All the design parameters were kept constant and the inlet (Co) and outlet (Ce) concentrations were monitored at regular time intervals until the adsorbent was completely exhausted. The results are shown in FIG. 20.

Example 6: Column Experiments with PFCs

Results

Figure 21A:
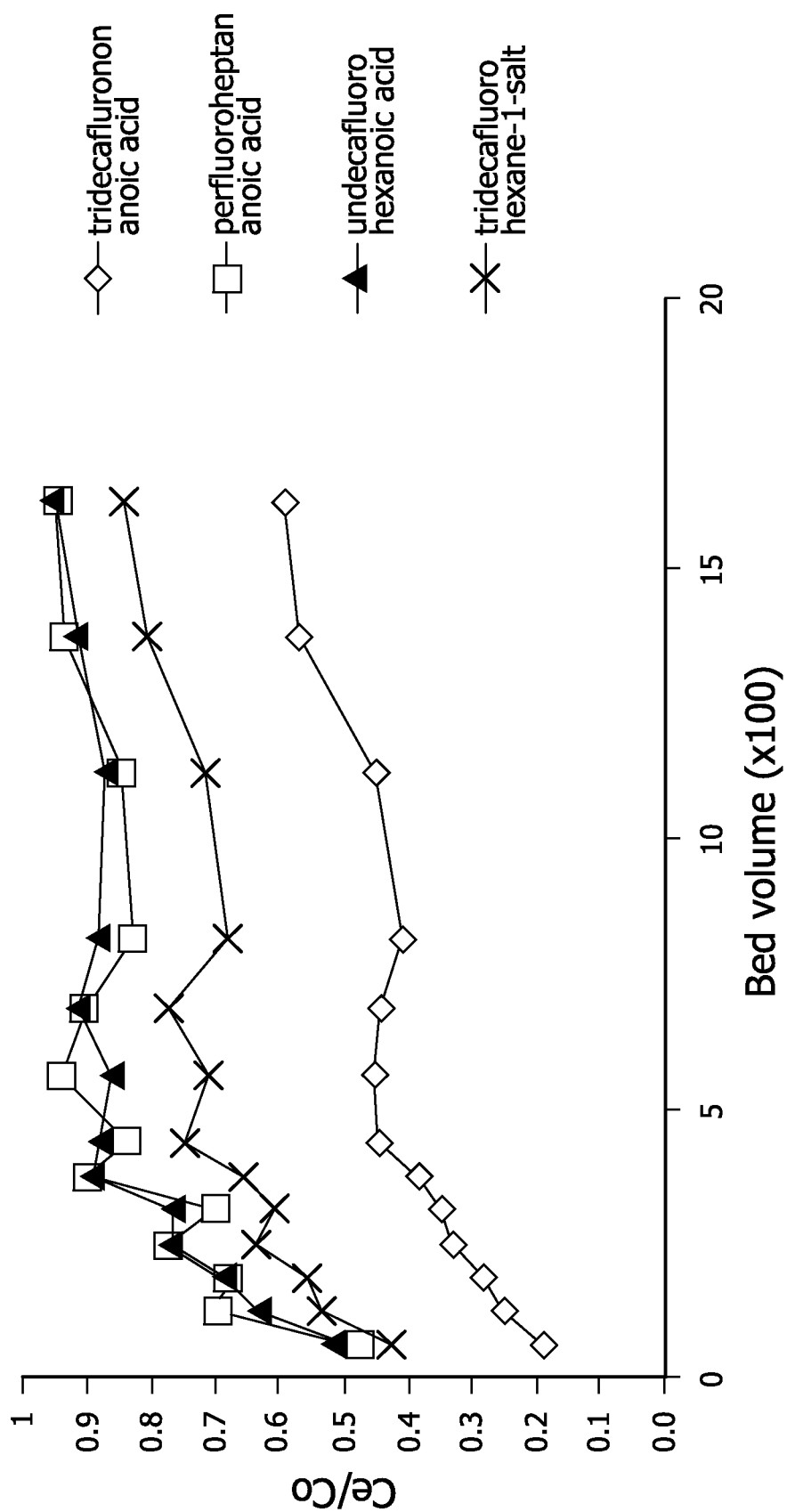
FIG. 21 illustrates removal of perfluorocarbons using adsorbent S4III from column experiments (initial concentration of each perfluorocarbon 50 μg/L).
Figure 21B:
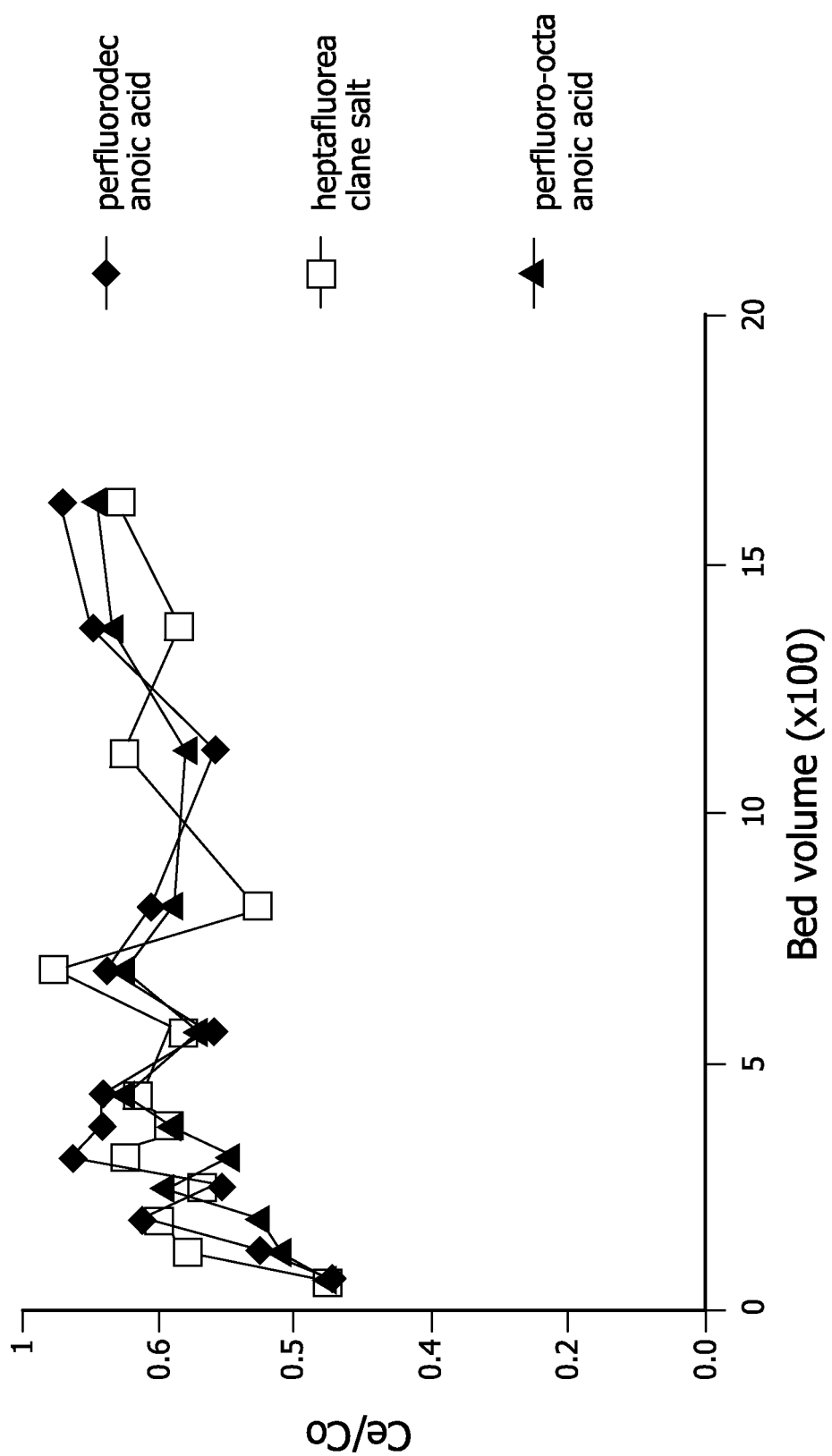

The same experimental conditions were used to perform column experiments with PFCs at an initial concentration of 50 μg/L. The results are summarized in FIG. 21.

Example 7: Regeneration Study

Results

A regeneration study was conducted with adsorbent S4 for the removal of PFOA at an initial concentration of 200 mg/L and at a dosage of 1.5 g/L. First of all, the sample was tested under batch conditions for 48 hours and the adsorption capacity was calculated based on the final concentration of PFOA. The used adsorbent was retained by filtration using 0.8 micron filter paper, washed with methanol, and dried at 80° C. for 15 hours. The adsorbent thus obtained was reused to conduct another batch experiment with the same concentration of the contaminant as mentioned before. All the experimental conditions were kept constant and the regeneration test was conducted for three successive runs.

Figure 22:
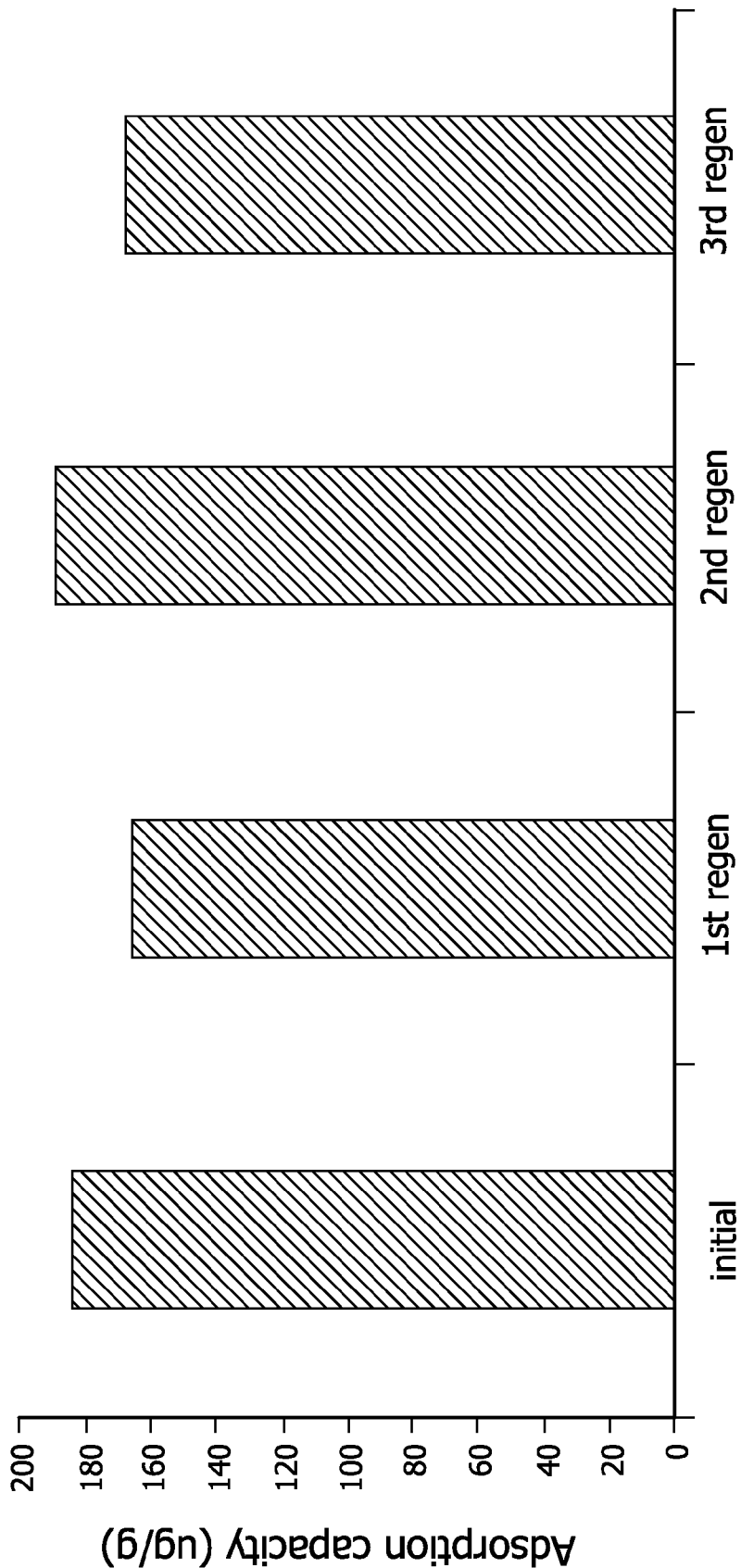
FIG. 22 illustrates a regeneration study of adsorbent S4 with PFOA (200 mg/L).

The results for the regeneration study showed that the adsorption capacity of the adsorbent was not significantly lost even after regeneration over three cycles (FIG. 22). However, weight loss of the adsorbent was observed, and was found to be about 10% over three cycles.

In conclusion, experimental results demonstrate that derivatized β-CDs supported onto silica particles are efficient for the removal of estrogens, BPA and PFOA from water.

What is claimed is:

1. Silica particles coated with cross-linked β-cyclodextrin polymer, wherein said cross-linked β-cyclodextrin polymer is the reaction product on silica particles of (i) β-cyclodextrin and hexamethylene diisocyanate in a molar ratio of β-cyclodextrin:hexamethylene diisocyanate of from about 1:7 to about 1:15, and wherein the molar ratio of β-cyclodextrin incorporated into said cross-linked β-cyclodextrin polymer to silica comprising the coated particles is from about 1:15 to about 1:30; or (ii) β-cyclodextrin and epichlorohydrin in a molar ratio of β-cyclodextrin:epichlorohydrin of from about 1:7 to about 1:9, and wherein the molar ratio of β-cyclodextrin incorporated into said cross-linked β-cyclodextrin polymer to silica comprising the coated particles is from about 1:83 to about 1:125.

2. The silica particles coated with cross-linked β-cyclodextrin polymer according to claim 1, wherein said cross-linked β-cyclodextrin polymer is the reaction product of β-cyclodextrin with hexamethylene diisocyanate.

3. The silica particles coated with β-cyclodextrin polymer according to claim 2 wherein the particle size is in the range from about US sieve size 10 to about US sieve size 200.

4. The silica particles coated with β-cyclodextrin polymer according to claim 1 wherein the particle size is in the range from about US sieve size 10 to about US sieve size 200.

5. A method of removing contaminants from a liquid comprising the step of contacting said liquid with the silica particles coated with β-cyclodextrin of claim 2.

6. The method of claim 5 wherein said contaminant is a steroid hormone.

7. The method of claim 5 wherein said contaminant is a phenol.

8. The method of claim 5 wherein said contaminant is a perfluorocompound.

9. A method of removing contaminants from a liquid comprising the step of contacting said liquid with the silica particles coated with β-cyclodextrin of claim 1.

10. The method of claim 9 wherein said liquid is flowing.

11. The method of claim 10 wherein said liquid is mixed with said silica particles coated with β-cyclodextrin and said mixture is agitated.

12. The method of claim 9 wherein said silica particles coated with β-cyclodextrin are contained in a column.

13. The method of claim 9 wherein said liquid is stationary.

14. The method of claim 13 wherein said liquid is mixed with said silica particles coated with β-cyclodextrin and said mixture is agitated.

15. The method of claim 9 wherein said contaminant is a steroid hormone.

16. The method of claim 15 wherein said steroid hormone is an estrogen, a progestrogen or a testosterone.

17. The method of claim 16 wherein said steroid hormone is selected from the group consisting of 17β-estradiol, 17α-ethynylestradiol, estriol, 17α-estradiol, trimegestrone, estrone, 17α-dihydroequilin, medrogestone, progesterone, gestodone, norgestrel, equilin, testosterone, desogestrel and etonorgestrel.

18. The method of claim 9 wherein said contaminant is a phenol.

19. The method of claim 18 wherein said phenol is bisphenol A (BPA).

20. The method of claim 9 wherein said contaminant is a perfluorocompound.

21. The method of claim 20 wherein said perfluorocompound is selected from the group consisting of tridecafluorononanoic acid, perfluoroheptanoic acid, undecafluorohexanoic acid, perfluorodecanoic acid, heptafluorooctane salt and perfluorooctanoic acid (PFOA).

22. A process for producing silica particles coated with β-cyclodextrin comprising:
coating silica particles with β-cyclodextrin; and
polymerizing said β-cyclodextrin with hexamethylene diisocyanate in a polymerization reaction to form hexamethylene diisocyanate-crosslinked β-cyclodextrin polymer;
wherein the molar ratio of β-cyclodextrin: hexamethylene diisocyanate in said polymerization reaction is from about 1:7 to about 1:15 and wherein the molar ratio of β-cyclodextrin:silica in said polymerization reaction is from about 1:15 to about 1:30.

23. A process for producing silica particles coated with β-cyclodextrin comprising:
coating silica particles with β-cyclodextrin; and
polymerizing said β-cyclodextrin with epichlorohydrin in a polymerization reaction to form epichlorohydrin-crosslinked β-cyclodextrin polymer;
wherein the molar ratio of β-cyclodextrin: epichlorohydrin in said polymerization reaction is from about 1:7 to about 1:9 and wherein the molar ratio of β-cyclodextrin:silica in said polymerization reaction is from about 1:83 to about 1:125.

* * * * *